(12) United States Patent
Almassian et al.

(10) Patent No.: US 8,658,677 B2
(45) Date of Patent: Feb. 25, 2014

(54) PYRIDYL-2-METHYLAMINO COMPOUNDS, COMPOSITIONS AND USES THEREOF

(75) Inventors: Bijan Almassian, Cheshire, CT (US); Martin J. Sadowski, New York, NY (US); Xu Kevin Lin, Branford, CT (US)

(73) Assignees: Aria Neurosciences Inc., Hamden, CT (US); New York University, New York, NY (US)

( * ) Notice: Subject to any disclaimer, the term of this patent is extended or adjusted under 35 U.S.C. 154(b) by 0 days.

(21) Appl. No.: 13/543,760

(22) Filed: Jul. 6, 2012

(65) Prior Publication Data

US 2013/0079376 A1    Mar. 28, 2013

Related U.S. Application Data

(60) Provisional application No. 61/505,511, filed on Jul. 7, 2011.

(51) Int. Cl.
*A61K 31/44* (2006.01)

(52) U.S. Cl.
USPC .......................................... 514/357; 514/395

(58) Field of Classification Search
USPC ................................................. 514/357, 395
See application file for complete search history.

(56) References Cited

U.S. PATENT DOCUMENTS 7,799,782 B2 * 9/2010 Munson et al. ............ 514/234.5

OTHER PUBLICATIONS

Alzheimer's & Dementia, "2009 Alzheimer's disease facts and figures," Alzheimer's Association, (2009) 5, pp. 234-270.
Cirrito, J.R., et al., "In vivo assessment of brain interstitial fluid with microdialysis reveals plaque-associated changes in amyloid-beta metabolism and half-life," J. Neurosci. (2003) 23, pp. 8844-8853.
Cirrito, J.r., et al., "Synaptic activity regulates interstitial fluid amyloid-beta levels in vivo," Neuron (2005) 48, pp. 913-922.
DeMattos, R.B., et al., "ApoE and clusterin cooperatively suppress A beta levels and deposition: Evidence that ApoE regulates extracellular A beta metabolism in vivo," (2004) Neuron 41, pp. 193-202.
Gong, Y.S., et al., "Alzheimer's disease-affected brain: Presence of oligomeric A beta ligands (ADDLs) suggests a molecular basis for reversible memory loss," (2003) Proc. Natl. Acad. Sci. USA 100, 18, pp. 10417-10422.
Hardy, J., et al., "Medicine—The amyloid hypothesis of Alzheimer's disease: Progress and problems on the road to therapeutics," (2002) Science 297, pp. 353-356.
Holtzman, D.M., "Alzheimer's disease: Moving towards a vaccine," (2008) Nature 454, pp. 418-420.
Kang, J., et al., "The precursor of Alzheimer's disease amyloid A4 protein resembles a cell-surface receptor," (1987) Nature 375, pp. 733-736.
Lansbury, Jr., P.T., et al., "Structural model for the β-amyloid fibril based on interstrand alignment of an antiparallel-sheet comprising a C-terminal peptide," (1995) Nature Struct. Biol. 2, pp. 990-998.

Lewis, J., et al., "Enhanced neurofibrillary degeneration in transgenic mice expressing mutant tau and APP," (2001) Science Mag, 293, pp. 1487-1491.
Lewis, J., et al., "Neurofibrillary tangles, amyotrophy and progressive motor disturbance in mice expressing mutant (P301L) tau protein," (2000) Nat. Genet. 25, pp. 402-405.
Permanne, B., et al., "Reduction of amyloid load and cerebral damage in a transgenic mouse model of Alzheimer's disease by treatment with a beta-sheet breaker peptide," (2002) FASEB J. 16, pp. U165-U188.
Radde, R., et al., "A beta 42-driven cerebral amyloidosis in transgenic mice reveals early and robust pathology," (2006) Embo Reports 7, pp. 940-946.
Soto, C., et al., "β-sheet breaker peptides inhibit fibrillogenesis in a rat brain model of amyloidosis: Implications for Alzheimer's therapy," (1998) Nat. Med. 4, pp. 822-826.
Takahashi, R.H., et al., "Oligomerization of Alzheimer's beta-amyloid within processes and synapses of cultured neurons and brain," (2004) J. Neurosci. 24, pp. 3592-3599.
Takahashi, R.H., et al., "Co-occurrence of Alzheimer's disease beta-amyloid and tau pathologies at synapses," (2010) Neurobiol Aging, 31, pp. 1145-1152.
Tanzi, R.E., et al., "Clearance of Alzheimer's Aβ peptide: The many roads to perdition," (2004) Neuron 43, pp. 605-608.
Garcia-Alloza, M., et al., "Characterization of amyloid deposition in the APPswe/PS1dE9 mouse model of Alzheimer disease," (2006) Neurobiol. Dis. 24, pp. 516-524.
Jankowsky, J.L., et al., "Mutant presenilins specifically elevate the levels of the 42 residue beta-amyloid peptide in vivo: evidence for augmentation of a 42-specific gamma secretase," (2004) Hum. Mol. Genet. 13, pp. 159-170.
Sadowski, M., et al., "A synthetic peptide blocking the apolipoprotein E/beta-amyloid binding mitigates beta-amyloid toxicity and fibril formation in vitro and reduces beta-amyloid plaques in transgenic mice," (2004) Am. J. Pathol. 165, pp. 937-948.
Sadowski, M., et al., "Amyloid-beta deposition is associated with decreased hippocampal glucose metabolism and spatial memory impairment in APP/PS1 mice," (2004) J. Neuropath. Exp. Neurol. 63, pp. 418-428.
Sadwoski, M., et al., "Blocking the apolipoprotein E/amyloid-beta interaction as a potential therapeutic approach for Alzheimer's disease," (2006) Proc. Natl. Acad. Sci. U. S. A 103, pp. 18787-18792.

* cited by examiner

*Primary Examiner* — Rei-tsang Shiao
(74) *Attorney, Agent, or Firm* — Klauber & Jackson LLC

(57) ABSTRACT

Compounds are provided according to formula I:

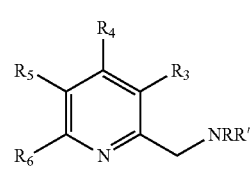

where R, R', $R_3$, $R_4$, $R_5$, and $R_6$ are as defined herein. Provided compounds and pharmaceutical compositions thereof are useful for the prevention and treatment of a variety of conditions in mammals including humans, including by way of non-limiting example, Alzheimer's Disease, Down's syndrome, Parkinson's Disease, and others.

19 Claims, 8 Drawing Sheets

PYRIDYL-2-METHYLAMINO COMPOUNDS, COMPOSITIONS AND USES THEREOF

RELATED APPLICATION

The present application claims the benefit under 35 U.S.C. §119 of U.S. Provisional Application Ser. No. 61/505,511, filed Jul. 7, 2011. The content of said provisional application is hereby incorporated by reference in its entirety.

FIELD

Provided herein are pyridylmethylamine compounds with anti-Aβ production, aggregation, inhibition of oxidative stress, and modulation of amyloid precursor protein (APP) translation properties, and pharmaceutical compositions thereof. Also provided are methods for preventing and/or treating medical conditions in mammals, such as neurodegenerative diseases including Alzheimer's, using the compounds and pharmaceutical compositions provided herein.

BACKGROUND

Pathogenesis of Alzheimer's disease (AD) is associated with accumulation of a hydrophobic β-amyloid (Aβ) peptide in the brain, which readily self-assembles into toxic oligomers and insoluble fibrils. Aβ oligomers are particularly destructive to excitatory synapses in the hippocampus as they bind to N-methyl-D-aspartic acid (NMDA) receptor proteins and cause their down regulation along with causing profound disturbances in synaptic morphology. In turn, Aβ fibrils form Aβ plaques, which are associated with deleterious activation of microglia and dystrophy of neurites passing along their vicinity. Long-term buildup of Aβ in the brain results in neurodegenerative cascade leading to widespread synaptic degeneration, formation of neurofibrillary tangles rand neuronal death resulting in occurrence of dementia in AD patients. Therefore, strategies modulating production, clearance and self-aggregation of Aβ are actively being pursued as disease modifying therapies.

Various agents can be used to treat medical conditions associated with AD.

However, despite the broad range of biological activities, the use of these agents has been limited by their toxicity at higher dose and lack of sufficient therapeutic efficacy at lower dose.

Thus, there remains a need to make new compounds which can have therapeutic efficacy for various neurodegenerative diseases including AD. The compounds, compositions, and methods described herein are directed toward this end.

SUMMARY OF THE INVENTION

In certain aspects, provided herein are pyridylmethylamine compounds with anti-Aβ production, aggregation, inhibition of oxidative stress, and modulation of amyloid precursor protein (APP) translation properties, and pharmaceutical compositions thereof. Also provided are methods for preventing and/or treating medical conditions in mammals, such as neurodegenerative diseases including Alzheimer's, using the compounds and pharmaceutical compositions provided herein.

In certain aspects, provided herein are pyridylmethylamine compounds useful for preventing and/or treating a broad range of neurodegenerative conditions, such as AD, Down's syndrome, Parkinson's and others.

In another aspect, provided here are methods for preventing, treating or ameliorating in a mammal various medical conditions, such as neurodegenerative conditions, which comprises administering to the mammal an effective medical condition treating amount of a pyridylmethylamine compound.

In one specific aspect, provided herein are method for preventing, treating or ameliorating in a mammal a medical condition, such as neurodegenerative conditions, which comprises administering to the mammal an effective medical condition treating amount of a compound according to formula I:

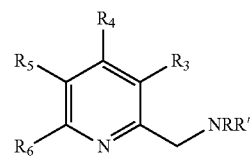

I or a pharmaceutically acceptable salt, solvate, hydrate, prodrug, stereoisomer, tautomer, isotopic variant, or N-oxide thereof, or a combination thereof;

wherein:

$R_3$, $R_4$, $R_5$ and $R_6$ are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, halogen, trihalomethyl, —CN, —NO$_2$, —NH$_2$, —OR$_1$, —NR$_1$R$_2$, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —C(O)R$_1$, —N(R$_2$)C(O)R$_2$, —N(R$_1$)CO$_2$R$_2$, —OC(O)NR$_1$R$_2$, —OC(O)R$_1$, and optionally substituted lower alkyl;

$R_1$ and $R_2$ are independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, and optionally substituted lower alkyl;

R is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —N(R$_1$)C(O)R$_2$, —N(R$_1$)CO$_2$R$_2$, —C(O)R$_1$, and optionally substituted lower alkyl;

R' is selected from the group having formula II:

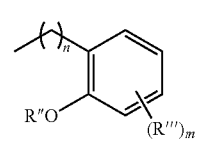

II wherein the subscript m is 1, 2, 3, or 4; the subscript n is 0, 1, 2, or 3;

R''' is selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, halogen, trihalomethyl, —CN, —NO$_2$, —NH$_2$, —OR$_1$, —NR$_1$R$_2$, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —C(O)R$_1$, —N(R$_1$)C(O)R$_2$, —N(R$_1$)CO$_2$R$_2$, OC(O)NR$_1$R$_2$, —OC(O)R$_1$, and optionally substituted lower alkyl;

R'' is H or substituted or unsubstituted $C_{1-8}$ alkyl or substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, trihalomethyl, or selected from the group having formula III:

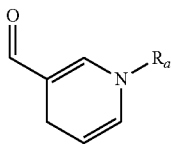

III wherein

R$_a$ is selected from the group consisting of hydrogen, halogen, substituted or unsubstituted $C_{1-8}$ alkyl, substituted or unsubstituted aryl, substituted or unsubstituted heteroaryl In one embodiment, with respect to the method, the medical condition is AD.

In other embodiment, the medical condition is Down's syndrome.

In other embodiment, the medical condition is Parkinson's disease.

In another specific aspect, provided herein are pharmaceutical compositions for preventing, treating or ameliorating in a mammal a medical condition, such as neurodegenerative conditions, which comprises a compound according to formula I:

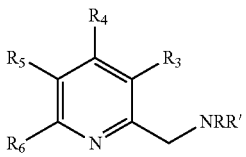

I or a pharmaceutically acceptable salt, solvate, hydrate, prodrug, stereoisomer, tautomer, isotopic variant, or N-oxide thereof, or a combination thereof;

wherein R, R', R$_3$, R$_4$, R$_5$, and R$_6$ are as described above.

In a specific aspect, provided herein is a pharmaceutical composition of a compound according to formula V:

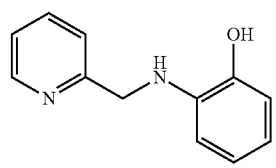

V or a pharmaceutically acceptable salt, solvate, hydrate, prodrug, stereoisomer, tautomer, isotopic variant, or N-oxide thereof, or a combination thereof.

The present invention further provides a method of treating a disease in a patient, where the disease is associated AD, by administering to the patient a therapeutically effective amount of a compound of formula I.

Other objects and advantages will become apparent to those skilled in the art from a consideration of the ensuing detailed description.

BRIEF DESCRIPTION OF THE DRAWINGS

FIG. 1(A) is a Thioflavin T fibrillization assay; FIG. 1(B) presents the results of TEM analysis; FIG. 1(C) shows the results of an oligomerization assay, FIG. 1(D) presents the principle of the assay; and FIG. 1(E) presents the results of a TEM assay.

DEFINITIONS

Chemical Definitions

Figure 1:
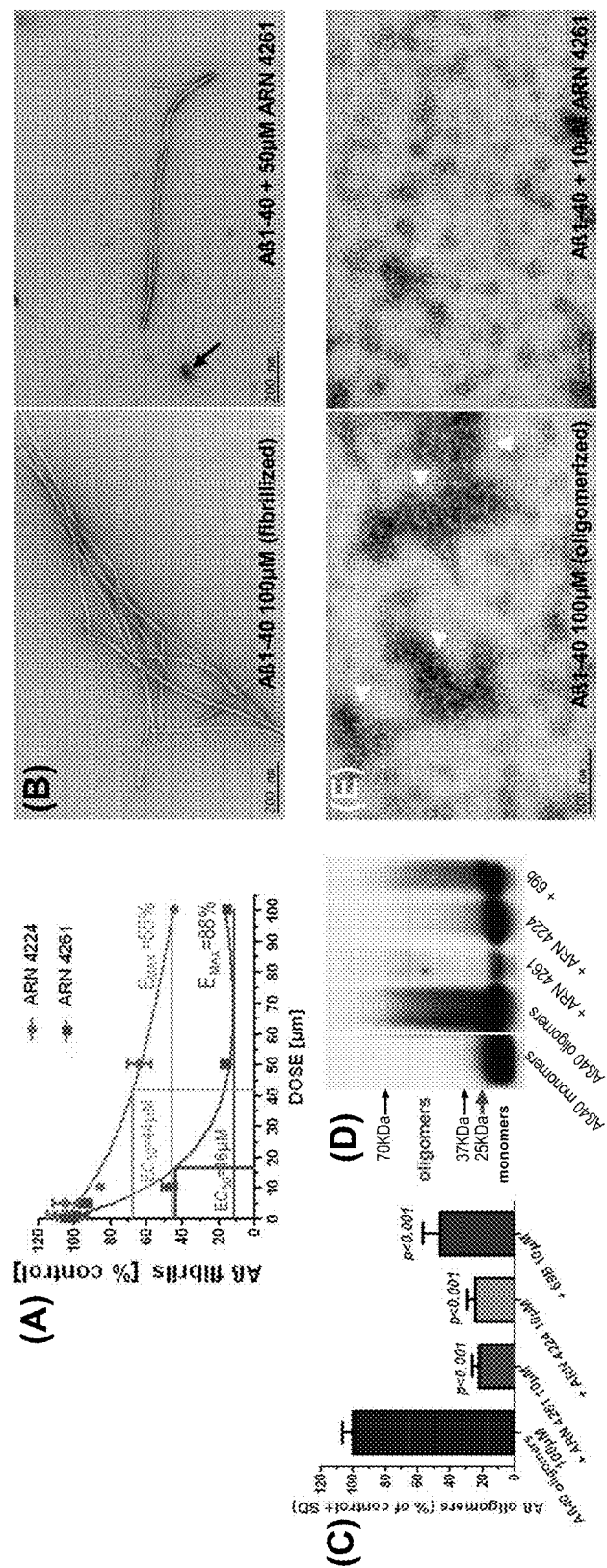
FIG. 1 presents a series of assays demonstrating the activity of compounds of the invention.

Definitions of specific functional groups and chemical terms are described in more detail below. The chemical elements are identified in accordance with the Periodic Table of the Elements, CAS version, *Handbook of Chemistry and Physics*, 75th Ed inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl.

"Alkylene" refers to a substituted or unsubstituted alkyl group, as defined above, wherein two hydrogens are removed to provide a divalent radical. Exemplary divalent alkylene groups include, but are not limited to, methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers a substituted or unsubstituted alkenyl group, as defined above, wherein two hydrogens are removed to provide a divalent radical. Exemplary divalent alkenylene groups include, but are not limited to, ethenylene (—CH=CH—), propenylenes (e.g., —CH=$CHCH_2$— and —C($CH_3$)=CH— and —CH=C($CH_3$)—) and the like.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers a substituted or unsubstituted alkynyl group, as defined above, wherein two hydrogens are removed to provide a divalent radical. Exemplary divalent alkynylene groups include, but are not limited to, ethynylene, propynylene, and the like.

"Aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

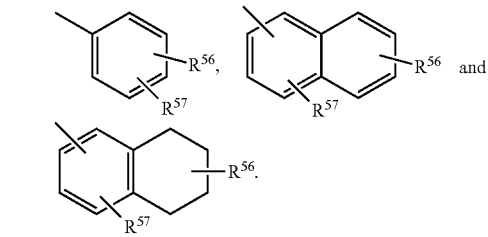

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl ring or with an aliphatic ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

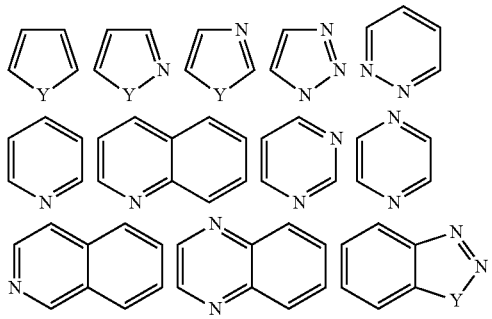

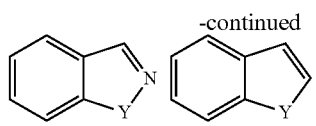

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

Examples of representative aryl having hetero atoms containing substitution include the following:

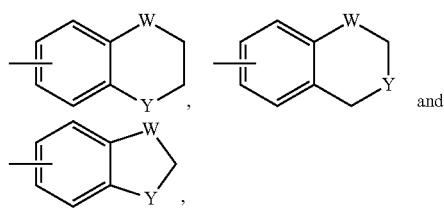

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3 to 10 membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8 membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

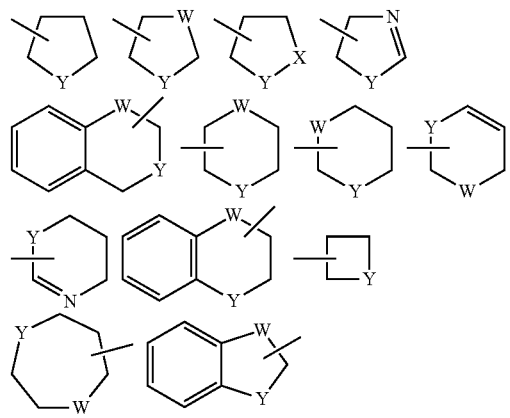

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more substituents selected from the group consisting of the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —$NR^{22}$C(O)$R^{23}$, where each instance of $R^{22}$ and R23 is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}$C(O)—$C_1$-$C_8$ alkyl, —$NR^{24}$C(O)—(CH$_2$)$_t$($C_6$-$C_{10}$ aryl), —$NR^{24}$C(O)—(CH$_2$)$_t$(5-10 membered heteroaryl), —$NR^{24}$C(O)—(CH$_2$)$_t$($C_3$-$C_{10}$ cycloalkyl), and —$NR^{24}$C(O)—(CH$_2$)$_t$(4-10 membered heterocyclyl), wherein t is an integer from 0 to 4, and each $R^{24}$ independently represents H or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$cycloalkyl, 4-10 membered heterocyclyl, $C_6$-$C_{10}$aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided that at least one of $R^{25}$ and $R^{26}$ is other than H.

"Acyloxy" refers to a radical —OC(O)$R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance, from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from: hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t(C_6$-$C_{10}$ aryl), —$(CH_2)_t$(5-10 membered heteroaryl), —$(CH_2)_t(C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted hydroxyalkyl, or unsubstituted $C_1$-$C_4$ haloalkoxy or hydroxy; or both $R^{38}$ groups are joined to form an alkylene group.

Exemplary 'substituted amino' groups are —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$—$(CH_2)_t(C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1$-$C_8$ alkyl, and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —$C(O)NH_2$.

"Substituted carbamoyl" or "substituted amido" refers to the radical —$C(O)N(R^{62})_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary 'substituted carbamoyl' groups include, but are not limited to, —C(O) $NR^{64}$—$C_1$-$C_8$ alkyl, —$C(O)NR^{64}$—$(CH_2)_t(C_6$-$C_{10}$ aryl), —$C(O)N^{64}$—$(CH_2)_t$(5-10 membered heteroaryl), —$C(O)NR^{64}$—$(CH_2)_t(C_3$-$C_{10}$ cycloalkyl), and —$C(O)NR^{64}$—$(CH_2)_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Carboxy' refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro. In further embodiments, the halo group is iodo.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(C=C)—.

"Ethylene" refers to substituted or unsubstituted —(C—C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —$C(=O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloropacyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —$S(=O)_2R^{aa}$) include, but are not limited to, p-toluenesulfonamide (Ts), benzenesulfonamide, 2,3,6,trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl (10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2one, 1-substituted 3,5-dinitro-4-pyridone, N-methylamine, N-allylamine, N-[2-(trimethylsilyl)ethoxy]methylamine (SEM), N-3-acetoxypropylamine, N-(1isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-pnitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3oxo-1-cyclohexenyl)amine, N-borane derivative, N-diphenylborinic acid derivative, N-[phenyl(pentaacylchromium or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, onitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $N(R^{bb})_2$, $-C(=O)SR^{aa}$, $-C(=O)R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyllmethoxyethyl, 1-methyl-1-benzyloxyethyl, 1-methyllbenzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, pchlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl pnitrophenyl carbonate, alkyl benzyl carbonate, alkyl p-methoxybenzyl carbonate, alkyl 3,4-dimethoxybenzyl carbonate, alkyl onitrobenzyl carbonate, alkyl p-nitrobenzyl carbonate, alkyl S-benzyl thiocarbonate, 4-ethoxylnaphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference.

"Compounds of the present invention", and equivalent expressions, are meant to embrace the compounds as herein-before described, in particular compounds according to any of the Formula herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

These and other exemplary substituents are described in more detail in the Detailed Description, Examples, and claims. The invention is not intended to be limited in any manner by the above exemplary listing of substituents.

Other Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like (see, e.g., Berge, et al., *J. Pharm. Sci.* 66(1): 1-79 (January '77).

"Pharmaceutically acceptable vehicle" refers to a diluent, adjuvant, excipient or carrier with which a compound of the invention is administered.

"Pharmaceutically acceptable metabolically cleavable group" refers to a group which is cleaved in vivo to yield the parent molecule of the structural Formula indicated herein. Examples of metabolically cleavable groups include —COR, —COOR,—CONRR and —CH$_2$OR radicals, where R is selected independently at each occurrence from alkyl, trialkylsilyl, carbocyclic aryl or carbocyclic aryl substituted with one or more of alkyl, halogen, hydroxy or alkoxy. Specific examples of representative metabolically cleavable groups include acetyl, methoxycarbonyl, benzoyl, methoxymethyl and trimethylsilyl groups.

"Prodrugs" refers to compounds, including derivatives of the compounds of the invention,which have cleavable groups and become by solvolysis or under physiological conditions the compounds of the invention that are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g., infant, child, adolescent) or adult subject (e.g., young adult, middleaged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human", "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Preventing" or "prevention" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Treating" or "treatment" of any disease or disorder refers, in certain embodiments, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is described by the R— and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, which are likewise formed by treatment with acid or base. Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure 5-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION OF THE PREFERRED EMBODIMENTS

In certain aspects, provided herein are pyridylmethylamine compounds anti-Aβ production, aggregation, inhibition of oxidative stress, and modulation of amyloid precursor protein (APP) translation properties, and pharmaceutical compositions thereof. Also provided are methods for preventing and/or treating medical conditions in mammals, such as neurodegenerative diseases including Alzheimer's, using the compounds and pharmaceutical compositions provided herein.

In certain aspects, provided herein are pyridylmethylamine compounds useful for preventing and/or treating a broad range of neurodegenerative conditions, such as AD, Down's syndrome, Parkinson's disease and others.

In another aspect, provided here are methods for preventing, treating or ameliorating in a mammal various medical conditions, such as neurodegenerative conditions, which comprises administering to the mammal an effective medical condition treating amount of a pyridylmethylamine compound.

In one specific aspect, provided herein are method for preventing, treating or ameliorating in a mammal a medical condition, such as neurodegenerative conditions, which comprises administering to the mammal an effective medical condition treating amount of a compound according to formula I:

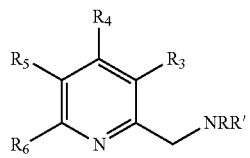

I or a pharmaceutically acceptable salt, solvate, hydrate, prodrug, stereoisomer, tautomer, isotopic variant, or N-oxide thereof, or a combination thereof;

wherein:

$R_3$, $R_4$, $R_5$ and $R_6$ are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, halogen, trihalomethyl, —CN, —NO$_2$, —NH$_2$, —OR$_1$, —NR$_1$R$_2$, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —C(O)R$_1$, —N(R$_1$)C(O)R$_2$, —N(R$_1$)CO$_2$R$_2$, —OC(O)NR$_1$R$_2$, —OC(O)R$_1$, and optionally substituted lower alkyl;

$R_1$ and $R_2$ are independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, and optionally substituted lower alkyl;

R is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —N(R$_1$)C(O)R$_2$, —N(R$_1$)CO$_2$R$_2$, —C(O)R$_1$, and optionally substituted lower alkyl;

R' is selected from the group having formula II:

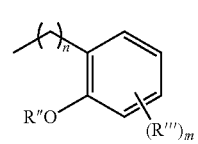

II wherein the subscript m is 1, 2, 3, or 4; the subscript n is 0, 1, 2, or 3;

R'' is selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, halogen, trihalomethyl, —CN, —NO$_2$, —NH$_2$, —OR$_1$, —NR$_1$R$_2$, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —C(O)R$_1$, —N(R$_1$)C(O)R$_2$, —N(R$_1$)CO$_2$R$_2$, OC(O)NR$_1$R$_2$, —OC(O)R$_1$, and optionally substituted lower alkyl;

R'' is H or substituted or unsubstituted $C_{1-8}$ alkyl or substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, trihalomethyl, or selected from the group having formula III:

III

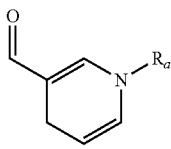

wherein
$R_a$ is selected from the group consisting of hydrogen, halogen, substituted or unsubstituted $C_{1-8}$ alkyl, substituted or unsubstituted aryl, substituted or unsubstituted heteroaryl In one embodiment, with respect to the method, the medical condition is AD.

In one embodiment, the medical condition is Down's syndrome.

In one embodiment, the medical condition is Parkinson's disease.

In one embodiment, with respect to the method, the medical condition is associated with modulation of Aβ production.

In one embodiment, with respect to the method, the medical condition is associated with inhibition of Aβ production.

In one embodiment, with respect to the method, the medical condition is associated with modulation of APP expression or APP translation.

In another specific aspect, provided herein are pharmaceutical compositions for preventing, treating or ameliorating in a mammal a medical condition, such as neurodegenerative conditions, which comprises a compound according to formula I:

I

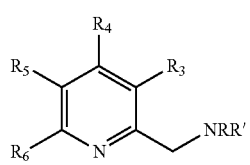

or a pharmaceutically acceptable salt, solvate, hydrate, prodrug, stereoisomer, tautomer, isotopic variant, or N-oxide thereof, or a combination thereof;

wherein R, R', $R_3$, $R_4$, $R_5$, and $R_6$ are as described above.

In one embodiment, with respect to the method or the pharmaceutical composition the compound is according to formula IVa or IVb:

IVa

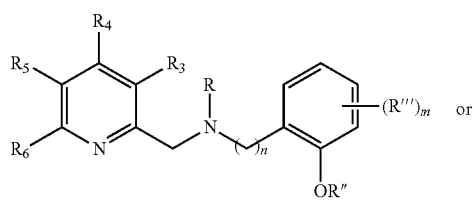

or

IVb

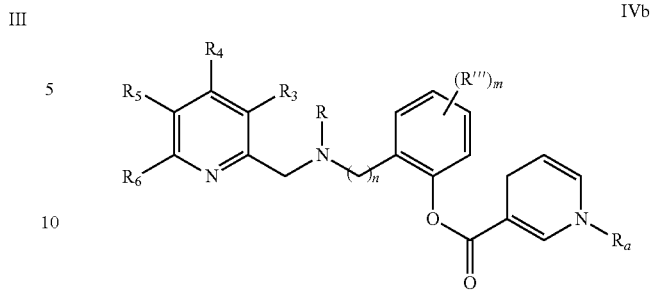

or a pharmaceutically acceptable salt, solvate, hydrate, prodrug, stereoisomer, tautomer, isotopic variant, or N-oxide thereof, or a combination thereof;
and wherein R, $R_a$, R", R''', $R_3$, $R_4$, $R_5$, $R_6$, m or n are as described for formula I.

In one embodiment, with respect to the formula IVa-IVb, the subscript n is 0 or 1.

In one embodiment, with respect to the formula I, IVa-IVb, R is H.

In one embodiment, with respect to the formula I, IVa-IVb, R" is H.

In one embodiment, with respect to the formula I, IVa-IVb, R''' is H.

In one embodiment, with respect to the formula I, IVa-IVb, $R_a$ is H.

In one embodiment, with respect to the formula I, IVa-IVb, $R_a$ is Me.

In one embodiment, with respect to the formula I, IVa-IVb, $R_3$ is H.

In one embodiment, with respect to the formula I, IVa-IVb, $R_4$ is H.

In one embodiment, with respect to the formula I, IVa-IVb, $R_5$ is H.

In one embodiment, with respect to the formula I, IVa-IVb, $R_6$ is H.

In one particular embodiment, with respect to the method or the pharmaceutical composition the compound is according to formula V:

V

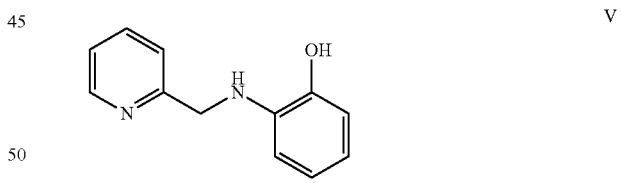

or a pharmaceutically acceptable salt, solvate, hydrate, prodrug, stereoisomer, tautomer, isotopic variant, or N-oxide thereof, or a combination thereof.

In one embodiment, with respect to the method or the pharmaceutical composition, the compound is a pharmaceutically acceptable salt.

In one embodiment, with respect to the method or the pharmaceutical composition, the compound is an acid salt.

In another specific aspect, provided herein are pharmaceutical compositions comprising a pharmaceutically acceptable carrier and a pharmaceutically effective amount of a compound of formula I, IVa-IVb, or V.

In one embodiment, with respect to the pharmaceutical composition the carrier is a parenteral carrier, oral or topical carrier.

In another specific aspect, provided herein are methods for preventing, treating or ameliorating in a mammal a medical condition, which comprises administering to the mammal an effective medical condition treating amount of a compound according to formula V:

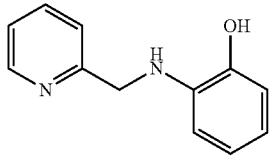

V or a pharmaceutically acceptable salt, solvate, hydrate, prodrug, stereoisomer, tautomer, isotopic variant, or N-oxide thereof, or a combination thereof.

In one embodiment, with respect to the method, the medical condition is Alzeimer's disease.

In one embodiment, the medical condition is Down's syndrome.

In one embodiment, the medical condition is Parkinson's disease.

In one embodiment, with respect to the method, the medical condition is associated with modulation of Aβ production.

In one embodiment, with respect to the method, the medical condition is associated with inhibition of Aβ production.

In one embodiment, with respect to the method, the medical condition is associated with modulation of APP expression or APP translation.

In another specific aspect, provided herein are methods for lowering the load of Aβ plaque, which comprises administering to the mammal an effective treating amount of a compound according to formula I, IVa, IVb, or V.

In another specific aspect, provided herein are methods for lowering the brain Aβ level, which comprises administering to the mammal an effective treating amount of a compound according to formula I, IVa, IVb, or V.

In one embodiment, with respect to the method, the compound is a pharmaceutically acceptable salt, solvate, hydrate, prodrug, stereoisomer, tautomer, isotopic variant, or N-oxide thereof, or a combination thereof of a compound according to any one of formula described herein.

In one particular embodiment, with respect to the compounds of formula I, IVa-IVb, or V, the compound is a pharmaceutically acceptable salt. In one particular embodiment, the salt is a quaternary salt.

In another aspect, the present invention provides a pharmaceutical composition comprising a pharmaceutically acceptable carrier and a pharmaceutically effective amount of a compound of compound of formula I, IVa-IVb, or V.

In one particular embodiment, with respect to the pharmaceutical formulation, the carrier is a parenteral carrier, oral or topical carrier.

In yet another aspect, the present invention provides a method for preventing, treating, ameliorating or managing a disease or condition which comprises administering to a patient in need of such prevention, treatment, amelioration or management, a prophylactically or therapeutically effective amount of a compound or pharmaceutical composition of compound of formula I, IVa-IVb, or V.

In one embodiment, the disease or condition is a neurological condition. In one embodiment, the disease or condition is neurodegeneration. In one embodiment, the disease or condition is AD.

In yet another aspect, the present invention provides a compound or pharmaceutical composition of compound of formula I, IVa-IVb, or V; or a pharmaceutically acceptable salt or solvate thereof for use as a pharmaceutical or a medicament.

In yet another aspect, the present invention provides a use of a compound of formula I, IVa-IVb, or V, or a pharmaceutically acceptable salt, solvate or composition thereof, for the manufacture of a medicament to treat a disease or condition associated with AD.

The present invention also relates to the pharmaceutically acceptable acid addition salts of compounds of formula I. The acids which are used to prepare the pharmaceutically acceptable salts are those which form non-toxic acid addition salts, i.e. slats containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate and the like.

In another aspect, the present invention provides pharmaceutical compositions comprising a pharmaceutically acceptable carrier and a pharmaceutically effective amount of a compound of formula I. In one embodiment, the carrier is a parenteral carrier, oral or topical carrier.

In yet another aspect, the present invention provides a method for preventing, treating, ameliorating or managing a disease or condition which comprises administering to a patient in need of such prevention, treatment, amelioration or management, a prophylactically or therapeutically effective amount of a compound of formula I, IVa-IVb, or V, or the pharmaceutical composition thereof.

In yet another aspect, the present invention provides a compound of formula I, IVa-IVb, or V or a pharmaceutically acceptable salt or solvate thereof for use as a pharmaceutical or a medicament.

In yet another aspect, the present invention provides a use of a compound of formula I, IVa-IVb, or V, or a pharmaceutically acceptable salt, solvate or composition thereof, for the manufacture of a medicament to treat a disease or condition associated with AD in mammal.

In yet another aspect, the present invention provides a method of treatment of a mammal, including a human being, to treat a disease for which a AD is indicated, including treating said mammal with an effective amount of a compound of formula I, IVa-IVb, or V, or with a pharmaceutically acceptable salt, solvate or composition thereof.

In yet another aspect, the present invention provides a combination of a compound of formula I, IVa-IVb, or V, and another pharmacologically active agent.

Additional embodiments within the scope provided herein are set forth in non-limiting fashion elsewhere herein and in the examples. It should be understood that these examples are for illustrative purposes only and are not to be construed as limiting in any manner.

Pharmaceutical Compositions

In another aspect, the invention provides a pharmaceutical composition comprising a pharmaceutically acceptable carrier and a pharmaceutically effective amount of a compound of Formula I.

When employed as pharmaceuticals, the compounds provided herein are typically administered in the form of a pharmaceutical composition. Such compositions can be prepared in a manner well known in the pharmaceutical art and comprise at least one active compound.

In certain embodiments, with respect to the pharmaceutical composition, the carrier is a parenteral carrier, oral or topical carrier.

The present invention also relates to a compound or pharmaceutical composition of compound according to Formula I; or a pharmaceutically acceptable salt or solvate thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of compounds of Formula I. In certain embodiments, the formulation comprises water. In another embodiment, the formulation comprises a cyclodextrin derivative. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salts of compounds of Formula I. The acids which are used to prepare the pharmaceutically acceptable salts are those which form non-toxic acid addition salts, i.e. salts containing pharmacologically acceptable aniovs such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Tablets

A compound of the invention may be admixed as a dry powder with a dry gelatin binder in an approximate 1:2 weight ratio. A minor amount of magnesium stearate is added as a lubricant. The mixture is formed into 10-500 mg tablets (1-250 mg of active compound per tablet) in a tablet press.

Formulation 7—Tablets

A compound of the invention may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Formulation 8—Tablets

A compound of the invention may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Formulation 9—Tablets

A compound of the invention may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Formulation 10—Tablets

A compound of the invention may be admixed as a dry powder with a dry gelatin binder in an approximate 1:2 weight ratio. A minor amount of magnesium stearate is added as a lubricant. The mixture is formed into 10-500 mg tablets (1-250 mg of active compound per tablet) in a tablet press.

Methods of Treatment

Alzheimer's disease (AD) causes dementia in 5.4 million patients in the USA. AD is a result of chronic and vast accumulation of a toxic and hydrophobic β-amyloid peptide (Aβ) peptide in the brain that drives synaptopathy, triggers the occurrence of neurofibrillary pathology and neuroinflammation, and associated neuronal loss. Early-onset, familial AD cases are linked to APP, presenilin (PS)1 or PS2 mutations, which either increase total Aβ production, or favor secretion of more toxic and aggregation prone Aβ42 at the expense of more soluble Aβ40. Reasons for Aβ accumulation in the more prevalent sporadic AD are less conspicuous, but likely are a combination of inherited features (e.g. apolipoprotein E isoform status) and acquired factors resulting in an age-progressing mismatch between production and clearance of Aβ.

Accumulation of Aβ is driven by its inherently low solubility and natural propensity to self-aggregate into toxic oligomers and insoluble fibrils. Aβ oligomers are particularly toxic to excitatory synapses on hippocampal neurons, while Aβ plaques are associated with deleterious activation of microglia and dystrophy of neurites. Furthermore, self aggregation of Aβ affects its clearance, which in turn further perpetuates brain Aβ accumulation. Aβ accumulation and resulting neurodegenerative cascade can predate by many years the prodromal amnestic symptoms seen in patients with mild cognitive impairment (MCI).

Development of therapies targeting the build up and toxicity of Aβ have been advocated as means of primary prevention (preclinical→MCI), secondary AD prevention (MCI→AD), and as a potential therapy applied during early stages of the disease when Aβ toxicity still plays a significant role, actively influencing progression of neurodegeneration. Among the pharmacological targets being pursued are drugs to reduce Aβ production (notably APP secretase inhibitors), to prevent Aβ aggregation, to reduce Aβ plaques (active immunization), and to promote Aβ clearance via passive immunotherapy or targeting BBB receptors for Aβ. Several compounds have been registered through IND process and tested in clinical trials, but thus far, no effective disease modifying agent for AD has received FDA approval. Failure of AD clinical trials thus far has been attributed to lack of adequate efficacy of tested compound in humans or their toxicity. For example, a γ secretase inhibitor Semagacestat (LY450139), showed a direct effect on Aβ production in human volunteers, but in the interim analysis of Phase III clinical trial was found to be associated with worsening of cognitive measures in AD patients and increased malignancy risk, likely due its off target effect on Notch-1 signaling pathway. Passive immunization appears to be the most clinically advanced and promising therapeutic approach for AD. Bapinezumab or intravenous immunoglobulins may be seeking FDA approval within the next few years. However, these drugs require constant and repetitive infusions, which would be a nuisance to the patients and increase cost of care. Given chronicity of AD pathogenesis, treatments targeting the Aβ cascade would likely need to be administered on a long-term basis. A need for well-tolerated, effective, orally administered anti-Aβ compounds remains unmet. Several second generation, orally available inhibitors of β and γ secretases are in development. However, it would still be necessary to demonstrate satisfactory effect in humans, without producing significant off target effects.

Aβ is a product of enzymatic cleavage of the amyloid precursor protein (APP) by β and γ secretases. Aβ production can be ameliorated by modulation of APP expression. Modulation of APP expression is unlikely to evoke off target effects of APP secretase inhibitors. Also it is unlikely to be associated with vasogenic complications of anti-Aβ passive immunization. While development of APP secretases inhibitors and anti-Aβ immunization approaches are widely pursued, very few molecules capable of modulating APP expression and showing drug development potential have been identified thus far. Furthermore, studies in AD Tg mice has indicated that modulation of APP expression and passive immunization can provide additive benefits on lowering Aβ load. Therefore, APP expression modulators constitute an underdeveloped, but promising approach for mono and combined AD therapy and prevention. This application proposes development of a novel class of APP modulators.

The compounds of the present invention are used as therapeutic agents for the treatment of conditions in mammals. In one particular aspect, these compounds can be used for the treatment of disease or condition related to neurological conditions. Specifically these compounds can be used for the treatment of disease or condition related to AD.

Accordingly, the compounds and pharmaceutical compositions provided herein find use as therapeutics for preventing and/or treating conditions including but not limited to AD, Parkinson's disease, Down's syndrome and others in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In a method of treatment aspect, provided herein is a method of treating a mammal susceptible to or afflicted with a condition associated with AD, which method comprises administering an effective amount of one or more of the pharmaceutical compositions just described.

In yet another method of treatment aspect, provided herein is a method of treating a subject susceptible to or afflicted with AD.

As a further aspect there is provided the present compounds for use as a pharmaceutical especially in the treatment or prevention of the aforementioned conditions and diseases. We also provide the use of the present compounds in the manufacture of a medicament for the treatment or prevention of one of the aforementioned conditions and diseases.

When used to prevent the onset of a neurological condition, the compounds provided herein will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds provided herein can be administered as the sole active agent or they can be administered in combination with other agents, including other active amines and derivatives. Administration in combination can proceed by any technique apparent to those of skill in the art including, for example, separate, sequential, concurrent and alternating administration.

General Synthetic Procedures

The compounds provided herein can be purchased or prepared from readily available starting materials using the following general methods and procedures. See, e.g., Synthetic Schemes below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography or HPLC. The following schemes are presented with details as to the preparation of representative substituted biarylamides that have been listed herein. The compounds provided herein may be prepared from known or commercially available starting materials and reagents by one skilled in the art of organic synthesis.

The enantiomerically pure compounds provided herein may be prepared according to any techniques known to those of skill in the art. For instance, they may be prepared by chiral or asymmetric synthesis from a suitable optically pure precursor or obtained from a racemate by any conventional technique, for example, by chromatographic resolution using a chiral column, TLC or by the preparation of diastereoisomers, separation thereof and regeneration of the desired enantiomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, NY, 1962); and S. H. Wilen *Tables of Resolving Agents and Optical Resolutions* 268 (E. L. Eliel ed., Univ. of Notre Dame Press, Notre Dame, Ind., 1972, *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.).

In certain embodiments, an enantiomerically pure compound of formula (1) may be obtained by reaction of the racemate with a suitable optically active acid or base. Suitable acids or bases include those described in Bighley et al., 1995, *Salt Forms of Drugs and Adsorption*, in *Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties.

Enantiomerically pure compounds can also be recovered either from the crystallized diastereomer or from the mother liquor, depending on the solubility properties of the particular acid resolving agent employed and the particular acid enantiomer used. The identity and optical purity of the particular compound so recovered can be determined by polarimetry or other analytical methods known in the art. The diasteroisomers can then be separated, for example, by chromatography or fractional crystallization, and the desired enantiomer regenerated by treatment with an appropriate base or acid. The other enantiomer may be obtained from the racemate in a similar manner or worked up from the liquors of the first separation.

In certain embodiments, enantiomerically pure compound can be separated from racemic compound by chiral chromatography. Various chiral columns and eluents for use in the separation of the enantiomers are available and suitable conditions for the separation can be empirically determined by methods known to one of skill in the art. Exemplary chiral columns available for use in the separation of the enantiomers provided herein include, but are not limited to CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

General processes for preparing compounds of formula (I) are provided as further embodiments of the invention and are illustrated in Scheme 1.

Scheme 1

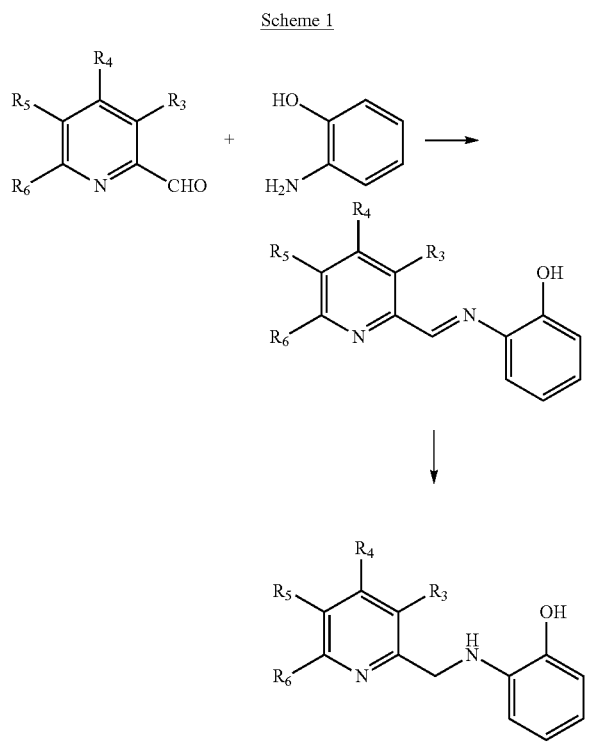

Synthesis of Representative Compounds

The syntheses of representative compounds of this invention can be carried out in accordance with the method set forth above and using the appropriate reagents, starting materials, and purification methods known to those skilled in the art.

Example 1

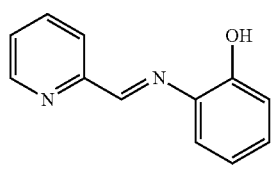

ARN4261

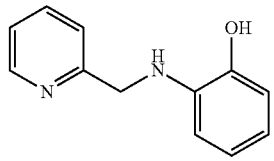

ARN2966

2-(Pyridin-2-ylmethyleneamino)-phenol (ARN4261)

2-Aminophenol (1.09 g, 10 mmol) was dissolved in ether (20 mL) and DCM (5 mL). 2-pyridinecaroxaldehyde (0.95 mL, 10 mmol) was added to the above solution. The reaction mixture was stirred at room temperature for 17 h; precipitate was formed. The light yellow solid (1.52 g, 77%) was filtered and dried. $^1$H (CDCl$_3$) δ 8.85 (s, 1H), 8.72 (d, J=3 Hz, 1H), 8.21 (d, J=9 Hz, 1H), 7.84 (t, J=7.5 Hz, 1H), 7.39 (t, J=7.5 Hz, 1H), 7.31 (bs, 1H), 7.25 (t, J=9 Hz, 1H), 7.04 (d, J=6 Hz, 1H), 6.94 (t, J=7.5 Hz, 1H), MS (M+H) 199.

2-[(pyridine-2-ylmethyl)-amino]-phenol (ARN 2966)

A mixture of 2-aminophenol (12.23 g, 112 mmol) and 2-pyridine carboxaldehyde (10.00 g, 93.4 mmol) in benzene (100 mL) was charged to a 250-mL round bottom flask equipped with Dean-Stark. The mixture was heated at reflux with magnetic stirring. In this course, water was collected and separated in the receiver by azeotropic distillation with benzene (more benzene could be added to the flask upon necessity). The reaction was stopped when no more water was distilled out as observed in the Dean-Stark receiver. The mixture was cooled to ambient temperature, and solvent was then removed by rotary evaporation. This crude material was used as such for the next reaction without further purification.

The crude material above was dissolved in methanol (400 mL), and cooled with an ice bath. Sodium borohydride (7.56 g, 200 mmol) was added in portions with care. After addition was complete, the mixture was allowed to warm up to room temperature and stirred for approximate 1 hr. When the reaction completion was monitored by TLC, the mixture was poured into ice water (1 L), and extracted by TBME (3×400 mL, solid was filtered whenever a phase-cut was difficult). The combined organic phase was dried over anhydrous sodium sulfate, and then filtered and concentrated. The residual material was purified by column chromatography on silica gel (ethyl acetate/hexanes 1:4 to 1:1), more than 7 g of brownish solid (37% overall yield) was obtained as pure product (HPLC purity>99%). $^1$H NMR (CDCl$_3$) δ 8.65 ppm (d, 1H), 7.75 ppm (t, 1H), 7.40 ppm (d, 1H), 7.30 ppm (m, 1H), 6.85 ppm (m, 2H), 6.75 ppm (m, 2H), and 4.55 ppm (s, 2H).

Assays

Compounds provided herein can be evaluated using various in vitro and in vivo assays known to those skilled in the art.

Example 2

Peptide Preparation

Synthetic Aβ 1-40 peptide (sequence: AEFRHDSGYEVHHQKLVFFAEDVGSNKGAIIGLMVGGVV) was synthesized at the W.M. Keck Foundation Facility (Yale University, New Haven, Conn.) by solid-phase technique on a p-methyl-benzhydrylamine resin, using a Biosearch SAM 2 synthesizer and purified by high performance liquid chromatography (HPLC) with the use of a reverse-phase support medium (Delta-Bondapak) on a 0.78×30 cm column with a 0-66% linear gradient of acetonitrile in 0.1% (v/v) trifluoroacetic acid, as previously described. The peptide content of the eluate was monitored by measurement of its absorption at 214 nm. To verify the sequence and purity of the peptide, linear, time-of-flight mass spectrometry was performed at the Skirball Institute at New York University. For aggregation studies the peptide was diluted in 1,1,1,3,3,3-hexafluoro-2-propanol (HFIP; Sigma St. Loius, Mo.) at a concentration of 10 mM/mL, aliquoted and lyophilized. HFIP treatment renders peptides monomeric with minimal β-sheet content. Lyophilized peptides were stored at −80° C. and resuspended immediately prior to each experiment in the appropriate diluent.

Example 3

Aggregation Experiment

The effect of compounds of the present invention on aggregation of Aβ 1-40 peptide was tested using a Thioflavin-T assay according to previously published methods. Aggregation of Aβ 1-40 incubated alone was measured for comparison. Aβ 1-40 was HFIP treated (as described above) and reconstituted in 100 mM Tris buffer (pH 7.4) to obtain a 100 µmol/L concentration. Stock of investigational compounds (50 mmol/L stock diluted in DMSO) was added to Aβ 1-40 to achieve of a concentration 10 or 100 µmol/L of investigational compound in 100 µmol/L of Aβ 1-40. All incubations were performed over a period of 7 days at 37° C. and the incubation mixture was slowly mixed for 6 hours every 24 h. At the conclusion of the experiment samples containing 15 µg of Aβ 1-40 with and without investigational compounds were added to 1 mL of 50 mM glycine, pH 9.2 and 2 µM of Thioflavin-T (Sigma Chemical, Co.; St. Louis, Mo.). Fluorescence was measured at an excitation of 435 nm and an emission of 485 nm in a Perkin-Elmer LS-50B fluorescence spectrophotometer (Perkin Elmer Instruments, Shelton, Conn.). A time scan of fluorescence was performed and three values after the decay reached a plateau (280, 290, 300 seconds) were averaged. The background fluorescence of 40 µL of Tris buffer added to 2 µM/L of Thioflavin-T solution was subtracted. Samples were run in duplicate. Differences in amount of fibrils formed in the presence of investigational compounds were evaluated by means of one-way ANOVA followed by a Dunnet post-hoc test using Statistica (version 6.1, StatSoft Inc., OK).

Example 4

Anti-Aβ Aggregation Properties of ARN4261

Our screen yielded two initial leads ARN4261 [(E)-2-(pyridin-2-ylmethylene-amino)phenol] and ARN4224 (C16H16N4O2; MW=296.3).

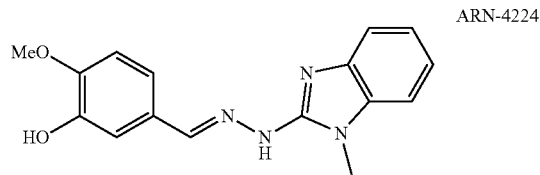 [SMILES: COc1ccc(/C=N/Nc2nc3ccccc3n2C)cc1O]

ARN4261 had stronger effect on Aβ fibrillization than ARN4224 while both compounds showed comparable effect on Aβ oligomerization.

As shown in FIG. 1, (A) Thioflavin-T fibrillization assay. 100 mM of HFIP monomerized synthetic Aβ40 was incubated in 0.1M Tris pH 7.0, T=37° C. for 8 days in the presence of 0-100 µM concentration of compounds. $E_{MAX}$ (% of maximal fibril reduction) and $EC_{50}$ were 88% and 16 µM for ARN4261, and 55% and 44 µM for ARN4224, respectively (B) Transmission electron microcopy (TEM) analysis confirmed that the ARN4261 treatment markedly reduced density and length of Aβ fibrils. An arrow indicates Aβ monomers clustered in ill developed protofibril. (C) Oligomerization assay. ARN4261 and ARN4224 reduced the amount of Aβ oligomers by 78% and 74%, respectively p<0.001. A compound 69b (GKLVFNmgA) was used as a positive control. 69b is homologous to Aβ sequence 17-21 and contains N-methyl glycine (Nmg), which renders it capable of anti-fibrillization and anti-oligomerization effect. (D) Principle of oligomerization assay. 100 µM Aβ40 was aggregated alone or with the addition of 10 µM of tested compounds [1:10 compound: Ab ratio] for 24 h in conditions promoting oligomers assembly, i.e., DMEM/F-12 medium+0.2% SDS, T=4° C. Prior to SDS-PAGE in non-reducing conditions samples were treated with glutaraldehyde. A strong smear of Aβ oligomers is seen between 37 and 70 KDa markers (arrows) in lane 2, and a dense band below the 25 KDa marker reflects Aβ monomers non-dissociated by 10% polyacrylamide gel. No oligomers above 37 KDa marker are seen in lane 1 containing only Aβ monomers run as a control. Lanes 3-5 show reduced amount of oligomers as a result of treatment with ARN4261, ARN4224, and 69b. (E) TEM of Aβ oligomers. White arrowheads indicate oligomers in a control samples whereas ARN4261 treatment increased number of Aβ monomers and dimers. Yellow arrowhead indicates smaller oligomers.

Example 5

Cell Culture Neurotoxicity Studies

The effect of 0.01-100 µmol/L concentrations of investigational compounds was tested on the viability of the N2a murine neuroblastoma cell line (American Type Culture Collection, Manassas, Va.). N2a cells were grown in Eagle's minimal essential medium with the addition of 10% fetal bovine serum, streptomycin and gentomycin (Sigma, St. Louis, Mo.), harvested with 2% trypsin and plated at 10,000 cells/100 µL per well in flatbottom, 96-well microtiter plates. The cells were allowed to attach to the plate overnight in an incubator (37° C., 5% CO$_2$) and in the following morning stocks of investigational compounds (50 mmol/L stock diluted in DMSO) were added to cells to achieve the final concentration 0.01-100 µmol/L. Adequate amounts of DMSO (Dimethyl sulfoxide, Sigma, St. Louis, Mo.) were added to control cells. Cells were grown in the presence of investigational compounds for 48 h and then their viability was assessed using a metabolic assay, which is based on cleavage of the yellow tetrazolium salt (MTT) to purple formazan crystals by viable cells. The MTT assay (Roche Molecular Biochemicals, Indianapolis, Ind.) was performed according to the manufacturer's instructions. The results from cell culture neurotoxicity studies were evaluated by one-way analysis of variance, followed by a Dunnett's test as a post hoc analysis.

Figure 2:
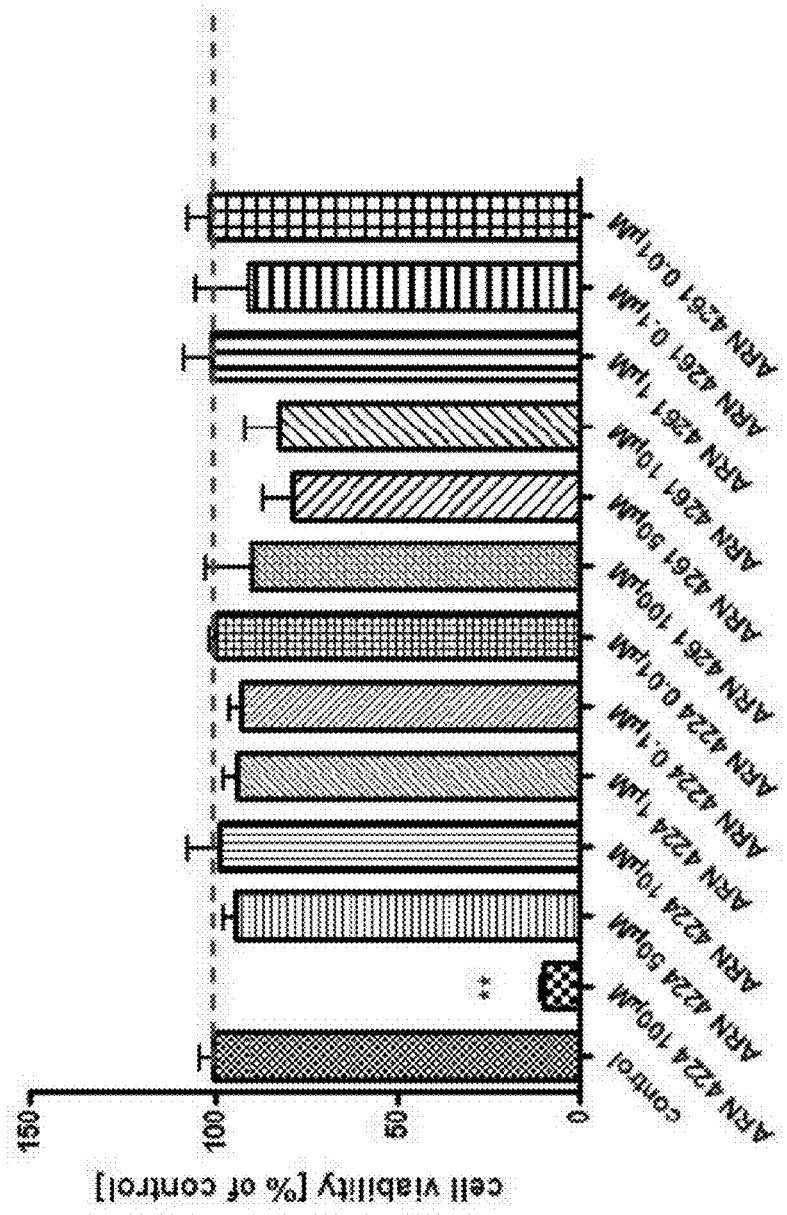
FIG. 2 presents the results of an MTT assay, to assess the viability of cells grown in the presence of compounds of the invention.

As shown in FIG. 2 (MTT assay), the compounds were tested for toxicity in SK-N-SH human neuroblastoma cells using MTT cell viability and LDH release (membrane integrity) assays. ARN4261 showed no toxicity in 0.1-100 µM concentrations, whereas 100 µM ARN4224 showed toxicity in both MTT and LDH release assays (not shown).

Example 6

Optimization of ARN4261 Structure for In Vivo Application Pharmacokinetic and BBB Permeability Studies Analysis of chemical structure stability revealed that ARN4261 is prone to self-decomposing and is easily degradable in acidic pH, hence is not suitable for oral administration. This is because of the instability of —C=N— bond. Therefore we have synthesized a reduced version of ARN4261 dubbed ARN2966 (2-[(pyridine-2-ylmethyl)-amino]-phenol, MW 200.2 Da, Log P 1.96). Surprisingly, ARN2966 was found to be not toxic, and in anti-Aβ aggregation assays it behaves comparably to ARN4261.

Pharmacokinetic characterization including BBB permeability of ARN2966 was performed in three months old, male CD-1 WT mice, which received a single oral (po; 25 mg/kg) or intravenous (iv; 5 mg/kg) dose of ARN2966 and were sacrificed 0.25, 0.5, 1, 2, 8, and 24 hr later (n=3 per time point). Plasma and brain concentration of ARN2966 were determined using liquid chromatography-mass spectrometry (LC/MS) (Table I). ARN2966 has a serum $t_{1/2}$ of 6.13 hr and achieved maximal brain concentration of 21.4 µg/kg (0.11 µM) after iv dosing. 64.2% of its orally administered dose was absorbed from the alimentary tract. As mentioned above, ARN4261 is prone to self-decomposing and is easily degradable in acidic pH, and hence is not suitable for oral administration. This is because of the instability of —CH=N— bond. Therefore, we focused on PK/BBB permeability characterization of ARN2966, where —CH=N— bond was reduced to —CH$_2$—NH—.

TABLE I

PK Properties of ARN 2966

| ARN 2966 Dose | Plasma | | | | | | Brain | | |
|---|---|---|---|---|---|---|---|---|---|
| | $t_{1/2}$ hr | $T_{max}$ hr | $C_{max}$ µg/L | $AUC_{(0-\infty)}$ µg/L*hr | $V_z$ L/kg | CL L/hr/kg | F* % | $T_{max}$ hr | $C_{max}$ µg/kg |
| IV - 5 mg/kg | 6.13 | 0.25 | 1031 ± 440 | 1229.78 | 35.97 | 4.07 | — | 0.25 | 21.4 ± 2.7 |
| PO - 25 mg/kg | 3.59 | 0.50 | 2658 ± 382 | 3947.65 | — | — | 64.20 | 0.50 | 12.5 ± 2.3 |

Abbreviations:
$t_{1/2}$ - half-life,
$T_{max}$ - time of occurrence for maximum drug concentration,
$C_{max}$ - maximum concentration,
$AUC_{(0-\infty)}$ area under curve,
$V_z$ - terminal phase volume of distribution,
CL - clearance,
F - fraction dose absorbed accounted for disparity between po and iv dose difference.
Data given as mean ±SD.

Example 7

ARN4261 and ARN2966 Reduce Aβ Production in Vitro

Figure 3:
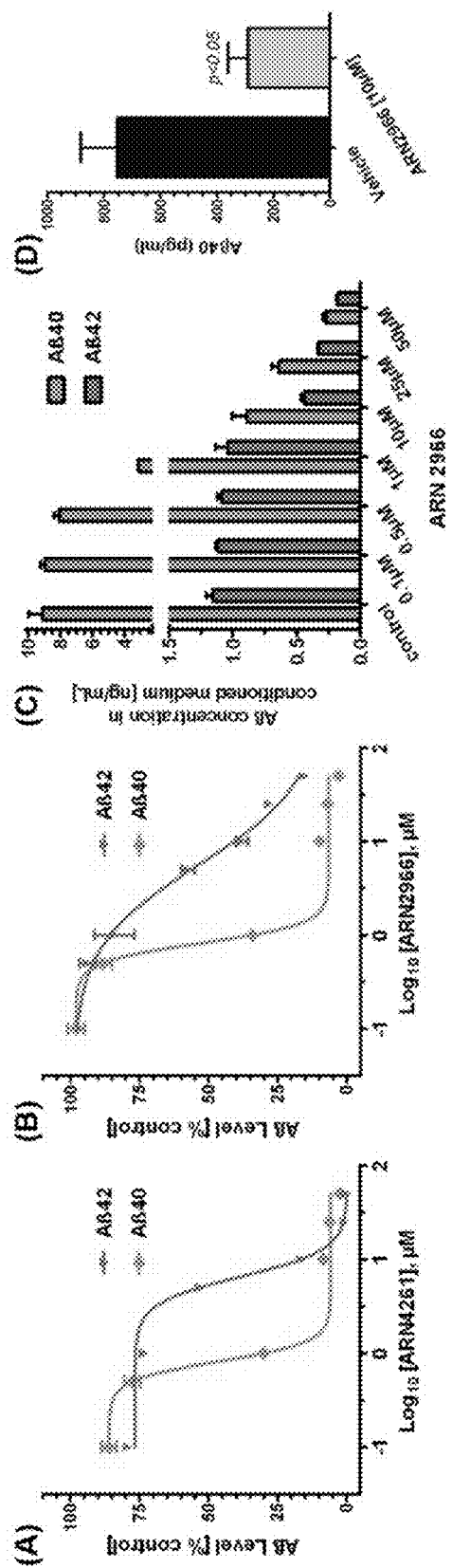
FIGS. 3A-3D demonstrate the results of incubation of the compounds of the invention with CHO clones transfected with WT human APP751 and double Swedish APP751 mutants.

In addition to studying the effect of ARN4261 and ARN2966 on Aβ oligomerization and fibrillization, we have explored their properties in respect to the modulation of Aβ production using CHO clones stably transfected with WT human APP751 and double Swedish APP751 mutant (KM670/671NL). The results in FIGS. 3(A) and 3(B) show inhibitory effect of ARN4261 and ARN2966 on secretion of Aβ40 and Aβ42 by 751APP$_{SW}$ CHO cells exposed to ARN compounds for 48 hr. Values are expressed as % of Aβ40 and Aβ42 levels in conditioned media (CM) of untreated cells. FIG. 3(C) Concentrations of Aβ40 and Aβ42 in 751APP$_{SW}$CHO cell CM under increasing concentrations of ARN2966. 751APP$_{SW}$CHO cells secrete Aβ40 and Aβ42 in proportions 9:1, akin to the proportions of Aβ peptides produced by neurons. FIG. 3(D) shows concentrations of Aβ40 in CM of vehicle and ARN2966 treated primary hippocampal neurons derived from Tg2576 AD Tg mice. Aβ40 and Aβ42 levels were determined using sandwich ELISA where C-terminal specific anti Aβ40 and Aβ42 mAbs were used as capture Abs and biotinylated 4G8 as the detection Ab. ARN4261 inhibited production of Aβ40 with IC$_{50\%}$=0.82 µM (95% confidence interval [CI] 0.76-0.88 µM) and E$_{MAX}$97.4±0.25%, and inhibited Aβ42 production with IC$_{50\%}$=6.54 µM (95% CI 6.2-6.97 µM) and E$_{MAX}$=98.9±0.4%. ARN2966 inhibited production of Aβ40 with IC$_{50\%}$=0.81 µM (95% CI 0.74-0.89 µM) and E$_{MAX}$97±0.3%, while Aβ42 with IC$_{50\%}$=5.53 µM (95% CI 3.99-7.71 µM) and E$_{MAX}$84.5%±0.7%. We also confirmed that ARN2966 inhibited secretion of Aβ by primary neuronal cultures derived from Tg2576 AD Tg mice. 10 µM ARN2966 lowered concentration of Aβ40 in the conditioned media by 61.4% (p<0.05).

Example 8

Figure 4:
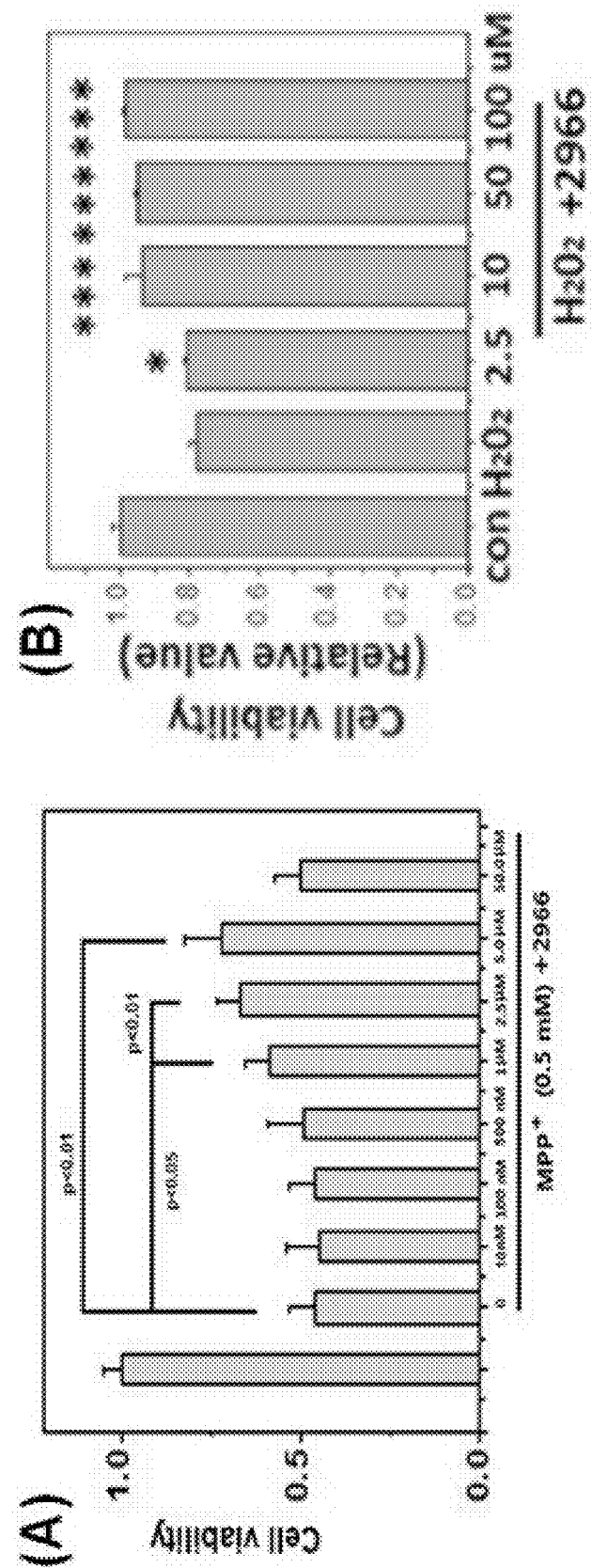
FIGS. 4(A) and 4(B) present the results of ex-vivo tests of the compounds to assess their effect on the viability of oxidatively challenged neural cells.

ARN2966 Rescues M17 Neuroblastoma Cells from Death Induced by MPP+ and H$_2$O$_2$ In addition to strong effects on Aβ production, ARN2966 has been shown ex vivo to confer improved viability to oxidatively challenged neural cells (FIG. 4).

FIG. 4(A) shows increasing concentrations of ARN2966 rescue M17 neuroblastoma cell death induced by MPP+ (0.5 mM 1-methyl-4-phenylpyridinium,) or (B) $H_2O_2$ (300 μM, right panel). Cell viability was detected by MTT assay. ARN2966 treatment restored normal cell morphology as determined by phase contrast microscopy, and reactive oxygen species (ROS) detection as studied with DCFH-DA.

Example 9

ARN2966 is not Toxic in vivo and Prevents Memory Deficit in $APP_{SW}/PS1_{dE9}$ AD Tg Mice Female $APP_{SW}/PS1_{dE9}$ mice received ARN2966 (n=10) or Vehicle (n=15) from the age of six to ten months. ARN2966 (50 mg/kg/day) was given once a day by intraperitoneal injection. During treatment, no noticeable changes in physical appearance, unprovoked behavior or response to external stimuli were observed. ARN2966-treated mice also showed proper rate of age related weight gain during the treatment (FIG. 5A). After conclusion of the experiments, samples of organs from ARN2966 and Vehicle treated animals were subjected to histopathological evaluation conducted by a veterinary pathologist. No signs of ARN2966 toxicity were reported. Signs of mild chronic peritonitis related to repeated daily intraperitoneal compound injection, however, were reported in both groups.

Figure 5:
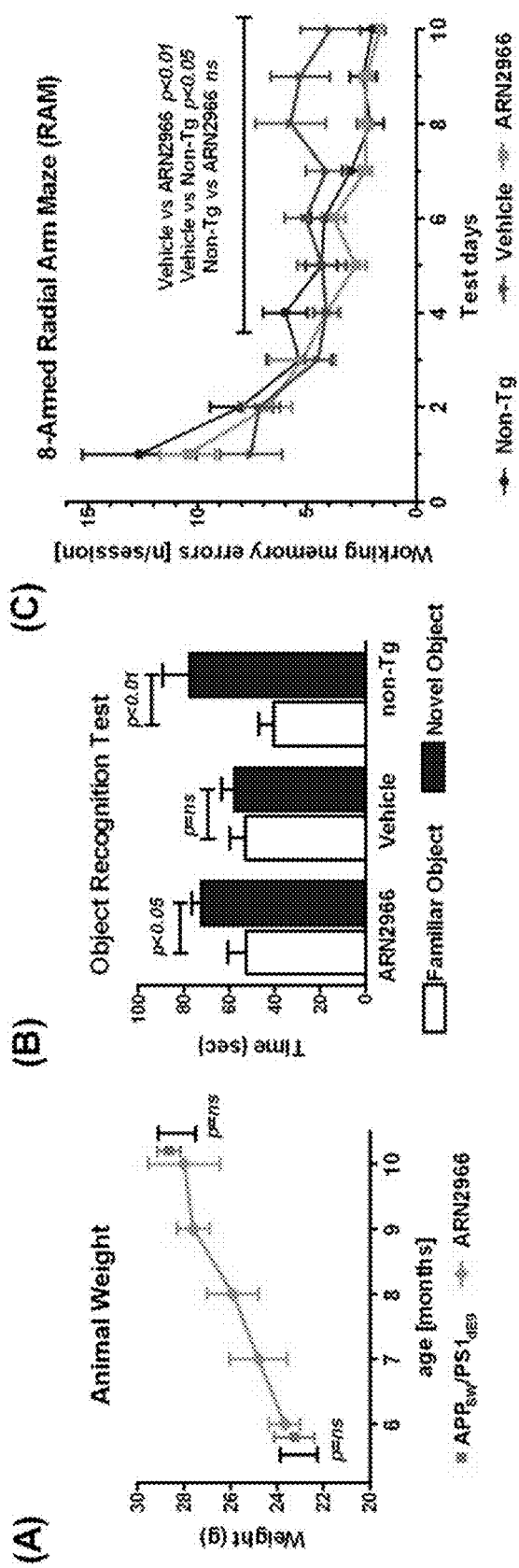
FIGS. 5(A)-5(C) present the results of the testing of APP$_{SW}$/PS1 $_{dE9}$ AD Tg mice to assess the effect of compounds of the invention on viability and memory deficit.

FIG. 5.(A) shows weight of female $APP_{SW}/PS1_{dE9}$ mice at the beginning and end of ARN2966 treatment is similar to that of sex and age matched untreated $APP_{SW}/PS1_{dE9}$ mice (red); p=ns, one-tailed unpaired t-test. FIG. 5.(B) shows object recognition test results, based on the inherent tendency of rodents to explore novel objects, are shown. ARN2966 treated $APP_{SW}/PS1_{dE9}$ and non-Tg mice spent significantly more time exploring the novel object while vehicle treated mice failed to distinguish between familiar and novel objects. P<0.05, unpaired, two-tailed t-test. FIG. 5.(C) shows radial Arm Maze. Mice explore 8-armed labyrinth, and results are displayed as a number of errors per session. One session is given per day. During the initial three days of testing, all animals made comparable number of errors while navigating through the labyrinth. Starting from day five, vehicle treated $APP_{SW}/PS1_{dE9}$ mice were consistently making more errors than ARN2966 treated $APP_{SW}/PS1_{dE9}$ and non-Tg littermates. One-way ANOVA p<0.001. Results of Newman-Keuls post-hoc analysis for days 4-10 are displayed on the graph.

During the last three weeks of treatment, animals were behaviorally tested using object recognition paradigm and the 8-armed radial arm maze, both of which measure memory capability. Akin to their non-Tg littermates, ARN2966 treated $APP_{SW}/PS1_{dE9}$ mice were able to distinguish a novel object from the familiar object they were exposed to during previous sessions (FIG. 5B). However, vehicle treated $APP_{SW}/PS1_{dE9}$ mice were incapable of discriminating between familiar and novel objects, as is characteristic of their phenotype. On the radial arm maze, ARN2966 group made fewer errors than vehicle group, and performed comparable to the non-Tg group (FIG. 5C). These results indicate that ARN2966 prevents memory deficit in $APP_{SW}/PS1_{dE9}$ mice and does not cause toxicity.

Example 10

ARN2966 Treatment Lowers Aβ Plaque Load

Figure 6:
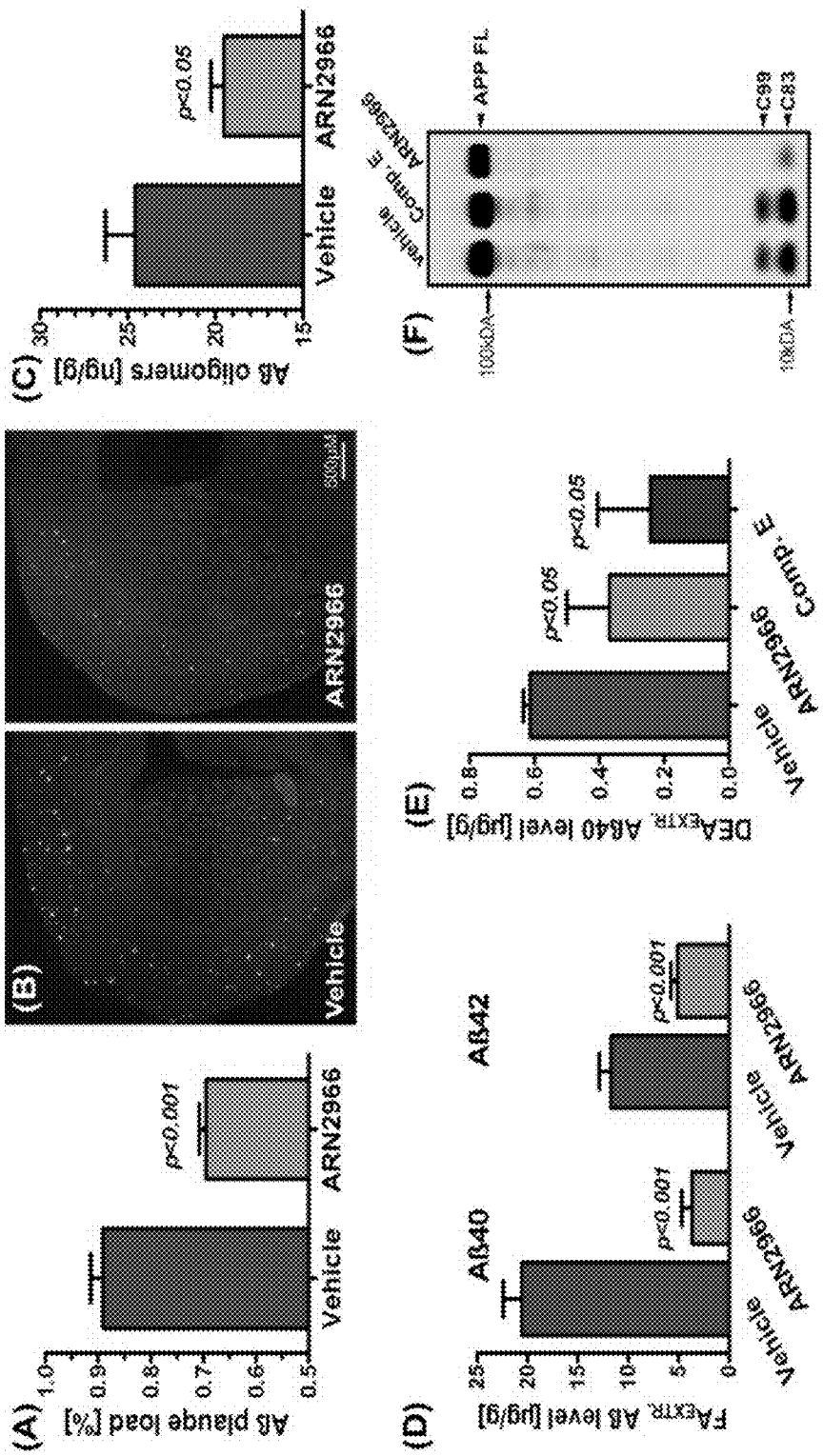
FIGS. 6(A)-6(F) present the results of the presence of compounds of the invention on the accumulation of Aβ brain plaques.

Female $APP_{SW}/PS1_{dE9}$ AD double transgenic (Tg) mice received daily intraperitoneal injections of ARN2966 (50 mg/kg) starting from the age of six months until the age of 10 months. Shown in FIG. 6 are example, Thioflavin-S brain sections from control (A) and (B) ARN2966 treated 10 month old, female $APP_{SW}/PS1_{dE9}$ revealing an apparent difference in the load of Aβ plaques. (C) Unbiased quantification of Aβ load revealed 25.8% reduction in the Aβ load under ARN2966 treatment (p<0.01, Mann Whitney U Test).

Example 11

ARN2966 Treatment Lowers Load of Aβ Plaque, and Brain Aβ Level

Figure 7:
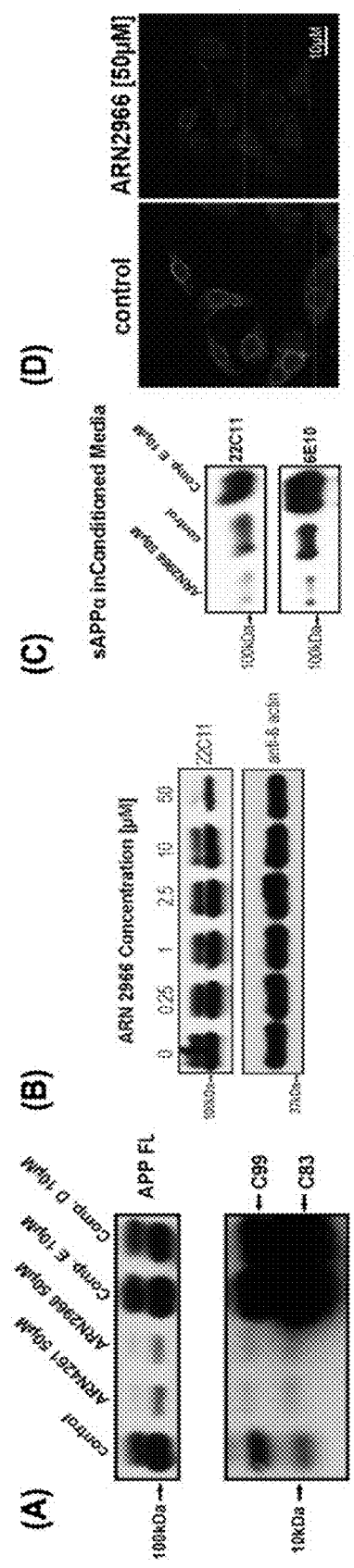
FIGS. 7(A)-7(D) present the results of tests that demonstrate that the compounds of the invention do not appear to modulate APP secretase activity.

Following the course of ARN2966 treatment, animals were sacrificed, and the load of Thioflavin-S (Th-S) stained Aβ plaques (% of histological section area covered by plaques) was quantified in the brain cortex on serial coronal sections through the rostrocaudal axis of the right hemisphere as described by us [Sadowski 2004]. The left hemisphere was homogenized (1:10 weight/volume), and aliquots of the homogenate were used to measure the level of Aβ oligomers (Aggregated β-Amyloid ELISA Kit, [Invitrogen]) or subjected to formic acid (FA) extraction to determine total Aβ40 and Aβ42 brain levels via sandwich ELISAs discriminating C-terminal configuration of both peptides as described by us [Sadowski 2006]. The load of Th-S positive plaques was reduced in the brain cortex of ARN2966 treated animals by 21.9% (p<0.001; FIGS. 6A, B), while the level of Aβ oligomers was reduced by 20.5% (p<0.05; FIG. 7C). Levels of FA extracted Aβ40 and Aβ42 were reduced by 82% (p<0.001) and 56% (p<0.001; FIG. 6C).

Furthermore, we conducted an acute treatment experiment where six months old female $APP_{SW}/PS1_{dE9}$ mice (n=3/group) were treated for five days with ARN2966 (50 mg/kg/day), Compound E (3 mg/kg/day) or Vehicle injected intraperitoneally. Mice were killed three hours after the last injections. The level of soluble Aβ40 was measured in the brain aliquots following diethylamine (DEA) extraction. It was lower in ARN2966 and Compound E treated groups by 39% (p<0.05) and 60% (p<0.05) comparing to vehicle treated mice, respectively (p<0.05; FIG. 6E). Furthermore, analysis of APP, C99, and C83 level on samples of brain homogenate subjected to SDS-PAGE and western immunoblotting showed evident reduction of APP, C99, and C83 signal in ARN2966 treated mice (p<0.05; FIG. 6F). A modest increase in C99 and C83 signal was also seen in Compound E treated animals. These results from the acute treatment experiment confirm the effect of ARN2966 on APP expression and Aβ production in vivo.

FIGS. 6.(A, B) ARN2966 treatment reduces load of Aβ plaques (n=10 ARN2966, n=15 Vehicle). (B) Representative photomicrograph of Th-S stained brain sections from vehicle and ARN2966 treated 10 month old, female $APP_{SW}/PS1_{dE9}$ reveal a difference in the load of Aβ plaques. (C) ELISA for aggregated human Aβ, revealing significant reduction in the Aβ-56-ligomers level in ARN2966 treated animals. (D) Reduced Aβ40 and Aβ42 levels in FA extracted brain homogenate, which represent the total brain content of Aβ peptides in ARN2966 treated animals (ELISA). (E) Reduced soluble Aβ40 level in DEA extracted brain homogenate, of ARN2966 and Compound E treated mice (ELISA). (F) Western immunoblot developed using anti-C terminal APP polyclonal Ab (1:500, Leinco, St. Louis, Mo.) demonstrating marked reduction in APP, C99, and C83 signal ARN2966 treated animals. Aβ concentrations in (C) (D) and (E) are given per gram of wet brain. All values are given as mean±SEM. Statistical analysis was done using two-tailed unpaired t-test, following confirmation of normal distribution of data using Shapiro-Wilk test.

Example 12

ARN4261 and ARN2966 Modulate APP Translation

Given that APP secretase inhibitors have encountered numerous setbacks during clinical development, it is important to point out that ARN4261 and ARN2966 do not appear to reduce Aβ production through modulating activity of APP secretases. As shown in FIGS. 7A, B, ARN4261 and ARN2966 reduce the level of full length APP (APP FL) and both C99 and C83 APP stubs resulting from B and a secretase cleavage of APP, respectively. For comparison, we show effects of treatment with established γ-secretase inhibitors Compound E (Comp. E) ((S,S)-2-[2-(3,5-difluorophenyl)-acetylamino]-N-(1-methyl-2-oxo-5-phenyl-2,3-dihydro-1H-benzo[e][1,4]diazepin-3-yl)-propionamide) and Compound D (Comp. D, aka DAPT-N-[N-(3,5-difluorophenacetyl)-L-alanyl]-S-phenylglycine t-butyl ester) which cause some accumulation of APP FL, and substantial accumulation of C99 and C83 (FIG. 7A). Secretion of sAPP to conditioned media was also reduced in cells treated with ARN2966 (FIG. 7C). Immunostaining with 22C11 anti-APP mAb of 751APP$_{SW}$ CHO cells treated with ARN2966 was also reduced without evidence of staining redistribution (FIG. 7D). Pulse labeling experiment showed significantly reduced incorporation of 35S-Methionine by APP during translation in 751APP$_{SW}$ CHO cells treated with ARN2966, while translation of β-actin remained unaltered (FIGS. 8A,B). No change in APP mRNA level was observed in ARN2966 treated 751APP$_{SW}$ CHO cells (FIG. 8C). These data collectively show a marked reduction in APP level, associated with reduced rate of APP translation, and preserved level of APP mRNA, providing solid evidence that ARN2966 is an APP translation modulator.

FIG. 7(A) shows reduced levels of full length APP (APP FL) and C99 and C83 APP stubs in cell lysates of 751APP$_{SW}$ CHO clone treated with ARN2966 or ARN4261. Treatment with γ-secretase inhibitors, Compound E and Compound D (DAPT), modestly increased the APP FL level and substantially increased levels of C83 and C99 (1:500 anti-C term APP poly. Ab, Leinco, St. Louis, Mo.). FIG. 7(B) shows reduced levels of APP FL in 751APP$_{SW}$ CHO clone under treatment with increasing concentration of ARN2966. Reduction in APP FL level is seen with ARN2966 concentrations ≥10 µM, while no apparent change in the level of β-actin is noticed. FIG. 7(C) shows reduced levels of sAPPα (immunoblotted with mAb 6E10 1:3,000) and total sAPP stub (immunoblotted with 22C11 N-terminal APP mAb; 1:1,000) in conditioned media of 751APP$_{SW}$ CHO clone treated with ARN2966 compared to control, untreated cells. Treatment with Compound E increased level of sAPP stubs in conditioned media. (D) Reduced anti-APP staining (22C11 mAb against N-term. APP) in 751APP$_{SW}$ CHO cells treated with ARN2966.

Figure 8:
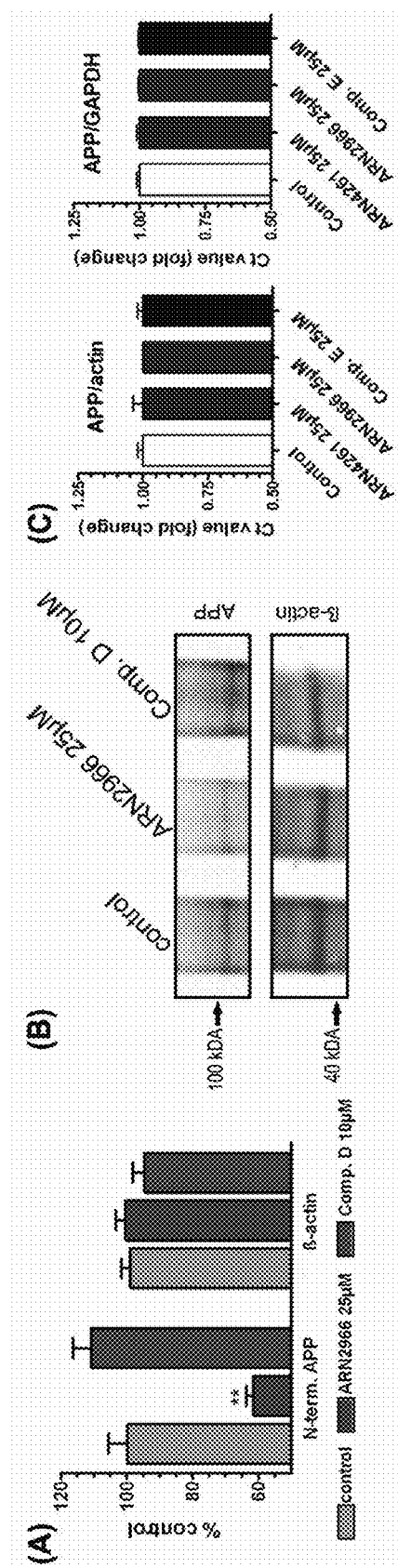
FIGS. 8(A)-8(C) present results that illustrate the effect of the compounds of the invention on APP translation.

FIGS. 8(A,B) shows radiolabeled APP and β-actin in 751APP$_{SW}$ CHO cells treated during the 2 h 35S-Methionine pulse with 25 µM ARN2966 or 10 µM Comp. D. APP was immunoprecipitated with 22C11 mAb against its N-terminus. Representative radiographs (B) and densitometric results averaged from three independent experiments are shown (A). Translation of APP was reduced by 61.5% (**p<0.01) during ARN2966 treatment. FIG. 8(C) shows mRNA levels for APP751$_{SW}$ in CHO cells treated with ARN4261, ARN2966, and Comp. E demonstrating lack of substantial effect of ARN compounds on APP transcription. Two sets of experiments were conducted using either actin or GAPDH as housekeeping genes.

References

Alzheimer's Association (2009). 2009 Alzheimer's disease facts and figures. Alzheimers. Dement. 5, 234-270.

Cirrito, J. R., May, P. C., O'Dell, M. A., Taylor, J. W., Parsadanian, M., Cramer, J. W., Audia, J. E., Nissen, J. S., Bales, K. R., Paul, S. M., DeMattos, R. B., and Holtzman, D. M. (2003). In vivo assessment of brain interstitial fluid with microdialysis reveals plaque-associated changes in amyloid-beta metabolism and half-life. J. Neurosci. 23, 8844-8853.

Cirrito, J. R., Yamada, K. A., Finn, M. B., Sloviter, R. S., Bales, K. R., May, P. C., Schoepp, D. D., Paul, S. M., Mennerick, S., and Holtzman, D. M. (2005). Synaptic activity regulates interstitial fluid amyloid-beta levels in vivo. Neuron 48, 913-922.

DeMattos, R. B., Cirrito, J. R., Parsadanian, M., May, P. C., O'Dell, M. A., Taylor, J. W., Harmony, J. A. K., Aronow, B. J., Bales, K. R., Paul, S. M., and Holtzman, D. M. (2004). ApoE and clusterin cooperatively suppress A beta levels and deposition: Evidence that ApoE regulates extracellular A beta metabolism in vivo. Neuron 41, 193-202.

Gong, Y. S., Chang, L., Viola, K. L., Lacor, P. N., Lambert, M. P., Finch, C. E., Krafft, G. A., and Klein, W. L. (2003). Alzheimer's disease-affected brain: Presence of oligomeric A beta ligands (ADDLs) suggests a molecular basis for reversible memory loss. Proc. Natl. Acad. Sci. USA 100, 10417-10422.

Hardy, J., and Selkoe, D. J. (2002). Medicine- The amyloid hypothesis of Alzheimer's disease: Progress and problems on the road to therapeutics. *Science* 297, 353-356.

Holtzman, D. M. (2008). Alzheimer's disease: Moving towards a vaccine. Nature 454, 418-420.

Kang, J., Lemaire, H. G., Unterbeck, A., Salbaum, J. M., Masters, C. L., Grzeschik, K. H., Multhaup, G., Beyreuther, K., and Muller-Hill, B. (1987). The precursor of Alzheimer's disease amyloid A4 protein resembles a cell-surface receptor. Nature 325, 733-736.

Lansbury, P. T., Costa, P. R., Griffiths, J. M., Simon, E. J., Auger, M., Halverson, K. J., Kocisko, D. A., Hendsch, Z. S., Ashburn, T. T., Spencer, R. G. S., Tidor, B., and Griffin, R. G. (1995). Structural model for the β-amyloid fibril based on interstrand alignment of an antiparallel-sheet comprising a C-terminal peptide. Nature Struct. Biol. 2, 990-998.

Lewis, J., Dickson, D., Lin, W. L., Chisholm, L., Corral, A., Jones, G., Yen, S. H., Sahara, N., Skipper, L., Yager, D., Eckman, C., Hardy, J., Hutton, M., and McGowan, E. (2001). Enhanced neurofibrillary degeneration in transgenic mice expressing mutant tau and APP. Nature, 293, 1487-1491.

Lewis, J., McGowan, E., Rockwood, J., Melrose, H., Nacharaju, P., Van Slegtenhorst, M., Gwinn-Hardy, K., Murphy, M. P., Baker, M., Yu, X., Duff, K., Hardy, J., Corral, A., Lin, W. L., Yen, S. H., Dickson, D., Davies, P., and Hutton, M. (2000). Neurofibrillary tangles, amyotrophy and progressive motor disturbance in mice expressing mutant (P301L) tau protein. Nat. Genet. 25, 402-405.

Permanne, B., Adessi, C., Saborio, G. P., Fraga, S., Frossard, M. J., Van Dorpe, J., Dewachter, I., Banks, W. A., Van Leuven, F., and Soto, C. (2002). Reduction of amyloid load and cerebral damage in a transgenic mouse model of Alzheimer's disease by treatment with a beta-sheet breaker peptide. FASEB J. 16, U165-U188.

Radde, R., Bolmont, T., Kaeser, S. A., Coomaraswamy, J., Lindau, D., Stoltze, L., Calhoun, M. E., Jaggi, F., Wolburg, H., Gengler, S., Haass, C., Ghetti, B., Czech, C., Holscher, C., Mathews, P. M., and Jucker, M. (2006). A beta 42-driven cerebral amyloidosis in transgenic mice reveals early and robust pathology. Embo Reports 7, 940-946.

Soto, C., Sigurdsson, E. M., Morelli, L., Kumar, A., Castalio, E. M., and Frangione, B. (1998). β-sheet breaker peptides inhibit fibrillogenesis in a rat brain model of amyloidosis: Implications for Alzheimer's therapy. Nat. Med. 4, 822-826.

Takahashi, R. H., Almeida, C. G., Kearney, P. F., Yu, F. M., Lin, M. T., Milner, T. A., and Gouras, G. K. (2004). Oligomerization of Alzheimer's beta-amyloid within processes and synapses of cultured neurons and brain. J. Neurosci. 24, 3592-3599.

Takahashi, R. H., Capetillo-Zarate, E., Lin, M. T., Milner, T. A., and Gouras, G. K. (2010). Co-occurrence of Alzheimer's disease beta-amyloid and tau pathologies at synapses. Neurobiol Aging, 31, 1145-1152.

Tanzi, R. E., Moir, R. D., and Wagner, S. L. (2004). Clearance of Alzheimer's Aβ peptide: The many roads to perdition. Neuron 43, 605-608.

M. Garcia-Alloza, E. M. Robbins, S. X. Zhang-Nunes, S. M. Purcell, R. A. Betensky, S. Raju, C. Prada, S. M. Greenberg, B. J. Bacskai, and M. P. Frosch, Characterization of amyloid deposition in the APPswe/PS1dE9 mouse model of Alzheimer disease, Neurobiol. Dis. 24 (2006) 516-524.

J. L. Jankowsky, D. J. Fadale, J. Anderson, G. M. Xu, V. Gonzales, N. A. Jenkins, N. G. Copeland, M. K. Lee, L. H. Younkin, S. L. Wagner, S. G. Younkin, and D. R. Borchelt, Mutant presenilins specifically elevate the levels of the 42 residue beta-amyloid peptide in vivo: evidence for augmentation of a 42-specific gamma secretase, Hum. Mol. Genet. 13 (2004) 159-170.

M. Sadowski, J.Pankiewicz, H. Scholtzova, J. A. Ripellino, Y. S. Li, S. D. Schmidt, P. M. Mathews, J. D. Fryer, D. M. Holtzman, E. M. Sigurdsson, and T. Wisniewski, A synthetic peptide blocking the apolipoprotein E/beta-amyloid binding mitigates beta-amyloid toxicity and fibril formation in vitro and reduces beta-amyloid plaques in transgenic mice, Am. J. Pathol. 165 (2004) 937-948

M. Sadowski, J. Pankiewicz, H. Scholtzova, J. Yong, D. Quartermain, C. H. Jensen, K. Duff, R. A. Nixon, R. J. Gruen, and T. Wisniewski, Amyloid-beta deposition is associated with decreased hippocampal glucose metabolism and spatial memory impairment in APP/PS1 mice, J. Neuropath. Exp. Neurol. 63 (2004) 418-428.

M. J. Sadowski, J. Pankiewicz, H. Scholtzova, P. D. Mehta, F. Prelli, D. Quartermain, and T. Wisniewski, Blocking the apolipoprotein E/amyloid-beta interaction as a potential therapeutic approach for Alzheimer's disease, Proc. Natl. Acad. Sci. U.S.A 103 (2006) 18787-18792

From the foregoing description, various modifications and changes in the compositions and methods provided herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A method for treating or ameliorating in a mammal a medical condition selected from Alzheimer's disease, Down's syndrome, and Parkinson's disease, which comprises administering to the mammal an effective medical condition treating amount of a compound according to formula I:

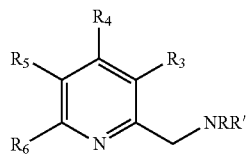

or a pharmaceutically acceptable salt, solvate, hydrate, prodrug, stereoisomer, tautomer, isotopic variant, or N-oxide thereof, or a combination thereof;

wherein:

$R_3$, $R_4$, $R_5$ and $R_6$ are independently selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, halogen, trihalomethyl, —CN, —NO$_2$, —NH$_2$, —OR$_1$, —NR$_1$R$_2$, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —C(O)R$_1$, —N(R$_1$)C(O)R$_2$, —N(R$_1$)CO$_2$R$_2$, —OC(O)NR$_1$R$_2$, —OC(O)R$_1$, and optionally substituted lower alkyl;

$R_1$ and $R_2$ are independently selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, and optionally substituted lower alkyl;

R is selected from the group consisting of hydrogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —N(R$_1$)C(O)R$_2$, —N(R$_1$)CO$_2$R$_2$, —C(O)R$_1$, and optionally substituted lower alkyl;

R' is selected from the group having formula II:

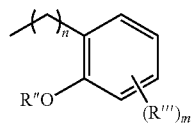

wherein the subscript m is 1, 2, 3, or 4; the subscript n is 0, 1, 2, or 3;

R''' is selected from the group consisting of hydrogen, halogen, substituted or unsubstituted $C_{1-8}$ alkyl, substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, halogen, trihalomethyl, —CN, —NO$_2$, —NH$_2$, —OR$_1$, —NR$_1$R$_2$, —S(O)$_{0-2}$R$_1$, —SO$_2$NR$_1$R$_2$, —CO$_2$R$_1$, —C(O)NR$_1$R$_2$, —N(R$_1$)SO$_2$R$_2$, —C(O)R$_1$, —N(R$_1$)C(O)R$_2$, —N(R$_1$)CO$_2$R$_2$, OC(O)NR$_1$R$_2$, —OC(O)R$_1$, and optionally substituted lower alkyl;

R'' is H or substituted or unsubstituted $C_{1-8}$ alkyl or substituted or unsubstituted $C_{2-8}$ alkenyl, substituted or unsubstituted $C_{2-8}$ alkynyl, substituted or unsubstituted aryl, substituted or unsubstituted heteroaryl, substituted or unsubstituted heterocyclyl, trihalomethyl, or selected from the group having formula III:

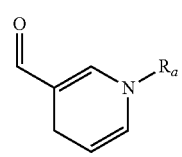

wherein $R_a$ is selected from the group consisting of hydrogen, halogen, substituted or unsubstituted $C_{1-8}$ alkyl, substituted or unsubstituted aryl, substituted or unsubstituted heteroaryl; and wherein the medical condition is a neurological disorder.

2. The method according to claim 1; wherein the compound is according to formula IVa or IVb:

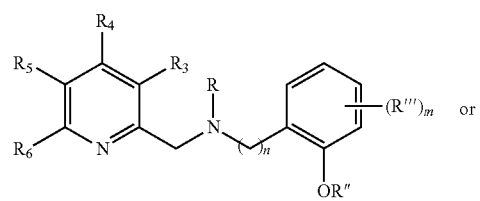

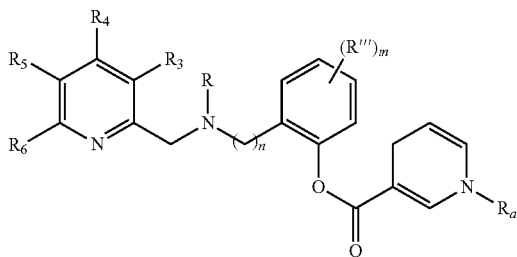

or a pharmaceutically acceptable salt, solvate, hydrate, prodrug, stereoisomer, tautomer, isotopic variant, or N-oxide thereof, or a combination thereof;

and wherein R, $R_a$, R", R'", $R_3$, $R_4$, $R_5$, $R_6$, m or n are as in claim 1.

3. The method according to claim 1; wherein R'" is H.
4. The method according to claim 1; wherein $R_a$ is H or Me.
5. The method according to claim 1; wherein $R_3$ is H.
6. The method according to claim 1; wherein $R_4$ is H.
7. The method according to claim 1; wherein $R_5$ is H.
8. The method according to claim 1; wherein $R_6$ is H.
9. The method according to claim 1; wherein the compound is according to formula V:

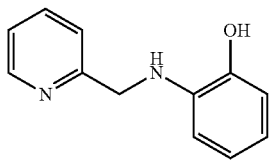

or a pharmaceutically acceptable salt, solvate, hydrate, prodrug, stereoisomer, tautomer, isotopic variant, or N-oxide thereof, or a combination thereof.

10. A method for treating or ameliorating in a mammal a medical condition selected from Alzheimer's disease, Down's syndrome, and Parkinson's disease, which comprises administering to the mammal an effective medical condition treating amount of a compound according to formula V:

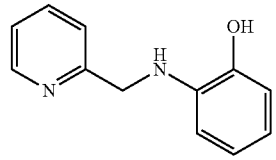

or a pharmaceutically acceptable salt, solvate, hydrate, prodrug, stereoisomer, tautomer, isotopic variant, or N-oxide thereof, or a combination thereof.

11. The method according to claim 1, wherein the medical condition is associated with modulation of Aβ production.
12. The method according to claim 1, wherein the medical condition is associated with inhibition of Aβ production.
13. The method according to claim 1, wherein the medical condition is associated with modulation of APP expression or APP translation.
14. A method for lowering the load of Aβ plaque, which comprises administering to the mammal an effective treating amount of a compound according to formula I of claim 1.
15. A method for lowering the brain Aβ level, which comprises administering to the mammal an effective treating amount of a compound according to formula I of claim 1.
16. A method for lowering the load of Aβ plaque, which comprises administering to the mammal an effective treating amount of a compound according to formula IVa or IVb of claim 2.
17. A method for lowering the load of Aβ plaque, which comprises administering to the mammal an effective treating amount of a compound according to formula V of claim 9.
18. A method for lowering the brain Aβ level, which comprises administering to the mammal an effective treating amount of a compound according to formula IVa or IVb of claim 2.
19. A method for lowering the brain Aβ level, which comprises administering to the mammal an effective treating amount of a compound according to formula V of claim 9.

* * * * *

SEQUENCE LISTING

```
<160> NUMBER OF SEQ ID NOS: 2

<210> SEQ ID NO 1
<211> LENGTH: 39
<212> TYPE: PRT
<213> ORGANISM: Artificial Sequence
<220> FEATURE:
<223> OTHER INFORMATION: Synthetic Abeta 1-40 peptide

<400> SEQUENCE: 1

Ala Glu Phe Arg His Asp Ser Gly Tyr Glu Val His His Gln Lys Leu
1               5                   10                  15

Val Phe Phe Ala Glu Asp Val Gly Ser Asn Lys Gly Ala Ile Ile Gly
            20                  25                  30

Leu Met Val Gly Gly Val Val
            35                  40

<210> SEQ ID NO 2
<211> LENGTH: 7
```

```
<212> TYPE: PRT
<213> ORGANISM: Synthetic peptide
<220> FEATURE:
<221> NAME/KEY: misc_feature
<222> LOCATION: 6
<223> OTHER INFORMATION: Xaa = N-methylglycine

<400> SEQUENCE: 2

Gly Lys Leu Val Phe Xaa Ala
1               5                   10
```